United States Patent
Ishikawa et al.

(10) Patent No.: US 8,728,770 B2
(45) Date of Patent: May 20, 2014

(54) METHOD FOR ENZYMATIC SACCHARIFICATION TREATMENT OF LIGNOCELLULOSE-CONTAINING BIOMASS, AND METHOD FOR PRODUCING ETHANOL FROM LIGNOCELLULOSE-CONTAINING BIOMASS

(75) Inventors: Kotaro Ishikawa, Tokyo (JP); Atsushi Furujyo, Kure (JP); Yaping Chao, Tokyo (JP); Hisako Tokuno, Tokyo (JP); Jun Sugiura, Kure (JP); Motohiro Matsumura, Tokyo (JP)

(73) Assignee: Oji Holdings Corporation, Tokyo (JP)

( * ) Notice: Subject to any disclaimer, the term of this patent is extended or adjusted under 35 U.S.C. 154(b) by 0 days.

(21) Appl. No.: 13/818,824

(22) PCT Filed: Aug. 31, 2011

(86) PCT No.: PCT/JP2011/069743
§ 371 (c)(1),
(2), (4) Date: Feb. 25, 2013

(87) PCT Pub. No.: WO2012/029842
PCT Pub. Date: Mar. 8, 2012

(65) Prior Publication Data
US 2013/0157318 A1 Jun. 20, 2013

(30) Foreign Application Priority Data

| Aug. 31, 2010 | (JP) | 2010-193310 |
| Nov. 15, 2010 | (JP) | 2010-254441 |
| Dec. 9, 2010 | (JP) | 2010-274235 |
| Mar. 30, 2011 | (JP) | 2011-075772 |
| May 13, 2011 | (JP) | 2011-107820 |
| Jun. 2, 2011 | (JP) | 2011-123976 |

(51) Int. Cl.
*C12P 19/14* (2006.01)

(52) U.S. Cl.
CPC .............................. *C12P 19/14* (2013.01)
USPC ............ 435/99; 435/100; 435/101; 435/105; 435/155; 435/165

(58) Field of Classification Search
None
See application file for complete search history.

(56) References Cited

U.S. PATENT DOCUMENTS

| 4,220,721 A | 9/1980 | Emert et al. |
| 5,196,069 A * | 3/1993 | Cullingford et al. ............ 127/37 |

(Continued)

FOREIGN PATENT DOCUMENTS

| CN | 101736630 A * | 6/2010 |
| JP | A-61-234790 | 10/1986 |

(Continued)

OTHER PUBLICATIONS

Ishihara et al., "Semicontinuous enzymatic hydrolysis of lignocelluloses", Biotechnology & Bioengineering, vol. 37, pp. 948-954, 1991.*

(Continued)

*Primary Examiner* — Rebecca Prouty
*Assistant Examiner* — Richard Ekstrom
(74) *Attorney, Agent, or Firm* — Knobbe Martens Olson & Bear LLP

(57) ABSTRACT

A method for the enzymatic saccharification of a lignocellulosic raw material, including adding a pretreated lignocellulosic raw material as a material suitable for an enzymatic saccharification reaction, together with an electrolyte containing a water-soluble salt, to water that contains a celluolose saccharification enzyme; saccharifying the raw material by an enzymatic saccharification reaction, as a suspension of the raw material having an electrical conductivity adjusted to 5-25 mS/cm; separating and recovering a reaction product and an enzyme-containing solution from the enzymatically saccharified treatment suspension; and recycling the recovered enzyme-containing solution as the enzyme for the enzymatic saccharification step.

8 Claims, 7 Drawing Sheets

(56) References Cited

U.S. PATENT DOCUMENTS

| | | | |
|---|---|---|---|
| 6,409,841 B1 * | 6/2002 | Lombard | 127/37 |
| 7,625,728 B2 * | 12/2009 | Eroma et al. | 435/158 |
| 8,030,030 B2 * | 10/2011 | Varanasi et al. | 435/72 |
| 8,110,383 B2 * | 2/2012 | Jonsson et al. | 435/161 |
| 8,338,139 B2 * | 12/2012 | Lali et al. | 435/96 |
| 8,399,228 B2 * | 3/2013 | Signes Nunez et al. | 435/165 |
| 2002/0197686 A1 * | 12/2002 | Lightner | 435/99 |
| 2004/0231060 A1 * | 11/2004 | Burdette et al. | 8/115.51 |
| 2007/0161095 A1 * | 7/2007 | Gurin | 435/134 |
| 2009/0004706 A1 * | 1/2009 | Vande Berg et al. | 435/128 |
| 2009/0061495 A1 * | 3/2009 | Beatty et al. | 435/165 |
| 2009/0117634 A1 * | 5/2009 | Bradley et al. | 435/165 |
| 2010/0015282 A1 * | 1/2010 | Mielenz et al. | 426/46 |
| 2010/0143974 A1 * | 6/2010 | Chung et al. | 435/72 |
| 2010/0273227 A1 * | 10/2010 | Jin et al. | 435/155 |
| 2011/0039311 A1 * | 2/2011 | Li et al. | 435/105 |
| 2011/0039319 A1 * | 2/2011 | Retsina et al. | 435/162 |
| 2011/0177567 A1 * | 7/2011 | Bakker et al. | 435/110 |
| 2011/0207177 A1 * | 8/2011 | Sugiura et al. | 435/72 |
| 2011/0314726 A1 * | 12/2011 | Jameel et al. | 44/451 |
| 2013/0005009 A1 * | 1/2013 | Mody et al. | 435/161 |

FOREIGN PATENT DOCUMENTS

| | | | |
|---|---|---|---|
| JP | A-63-087994 | | 4/1988 |
| JP | A-2005-168335 | | 6/2005 |
| JP | 200687319 A | * | 4/2006 |
| JP | A-2008-054676 | | 3/2008 |
| JP | A-2009-106932 | | 5/2009 |
| JP | 201017084 A | * | 1/2010 |
| JP | B-4447148 | | 4/2010 |
| JP | A-2010-098951 | | 5/2010 |
| JP | A-2011-041493 | | 3/2011 |

OTHER PUBLICATIONS

Scott et al., "An advanced bioprocessing concept for the conversion of waste paper to ethanol", Applied Biochemistry and Biotechnology, vol. 45/46, pp. 641-653, 1994.*

Deshpande M.V., et al., "Reutilization of enzymes for saccharification of lignocellulosic materials" Enzyme Microb. Technol., vol. 6, pp. 338-340, Aug. 1984.

International Search Report mailed on Nov. 8, 2011 in corresponding International Application No. PCT/JP2011/069743.

* cited by examiner

METHOD FOR ENZYMATIC SACCHARIFICATION TREATMENT OF LIGNOCELLULOSE-CONTAINING BIOMASS, AND METHOD FOR PRODUCING ETHANOL FROM LIGNOCELLULOSE-CONTAINING BIOMASS

This application is the U.S. National Phase under 35 U.S.C. §371 of International Application PCT/JP2011/069743, filed Aug. 31, 2011, designating the U.S., and published in Japanese as WO 2012/029842 on Mar. 8, 2012, which claims priority to Japanese Patent Application No. 2010-193310, filed Aug. 31, 2010; Japanese Patent Application No. 2010-254441, filed Nov. 15, 2010; Japanese Patent Application No. 2010-274235, filed Dec. 9, 2010; Japanese Patent Application No. 2011-075772, filed Mar. 30, 2011; Japanese Patent Application No. 2011-107820, filed May 13, 2011; and Japanese Patent Application No. 2011-123976, filed Jun. 2, 2011, the contents of which are incorporated herein by reference in their entireties.

TECHNICAL FIELD

The present invention relates to a method for the enzymatic saccharification treatment of a lignocellulose-based raw material or a method for the production of ethanol from a lignocellulose-based raw material, both methods having a pretreatment step of subjecting a lignocellulose-based raw material to a treatment for converting the lignocellulose-based raw material to a raw material appropriate for an enzymatic saccharification reaction; and an enzymatic saccharification step of saccharifying a pretreated lignocellulose-based raw material with an enzyme. More particularly, the invention relates to a method for the enzymatic saccharification treatment of a lignocellulose-based biomass, the method including a reaction of saccharifying a biomass containing lignocellulose that have been subjected to a treatment appropriate for saccharification, using a group of enzymes consisting of cellulolytic enzymes or hemicellulolytic enzymes, and the method making it possible to recover the group of enzymes used with a high recovery ratio and to recycle the group of enzymes over a long time period; or a method for the production of ethanol from a biomass containing lignocellulose, the method making it possible to increase the ethanol output by recovering fine fibers that remain in the treated suspension after a parallel saccharifying fermentation treatment, and subjecting the recovered fine fibers again to a saccharification treatment or a parallel saccharifying fermentation treatment.

Priority is claimed on Japanese Patent Application No. 2010-193310, filed Aug. 31, 2010; Japanese Patent Application No. 2010-254441, filed Nov. 15, 2010; Japanese Patent Application No. 2010-274235, filed Dec. 9, 2010; Japanese Patent Application No. 2011-075772, filed Mar. 30, 2011; Japanese Patent Application No. 2011-107820, filed May 13, 2011; and Japanese Patent Application No. 2011-123976, filed Jun. 2, 2011, the contents of which are incorporated herein by reference.

BACKGROUND ART

A technology of producing saccharides from a lignocellulose raw material that has been subjected to a treatment appropriate for saccharification, is a technology beneficial to the formation of a recycling-oriented society since alcohols that may be used as a gasoline substitute fuel, or chemical raw materials such as succinic acid and lactic acid that may be used as raw materials for plastics can be produced by using the saccharides as the fermentation substrates for microorganisms.

Methods for producing monosaccharides or oligosaccharides that may be used as fermentation substrates from the polysaccharides in a plant-based biomass, can be broadly classified into two types. One type is an acid saccharification method of hydrolyzing polysaccharides using a mineral acid, and the other type is an enzymatic saccharification method of hydrolyzing polysaccharides using an enzyme or a microorganism which produces the enzyme.

The acid saccharification method is technically complete as compared with the enzymatic saccharification method. However, in the case of the method of using a lignocellulose-based biomass as a raw material, the saccharide yield is low as compared with the method of using starch or molasses as a raw material, and also, the fact that a facility for treating waste acids discharged from treatment processes, or a large-sized facility capable of enduring the corrosion caused by acid is needed, causes an increase in the product cost, so that these pose a serious problem for practical application.

On the other hand, in regard to the enzymatic saccharification method, due to the decrease in the price of enzymes in recent years and the progress of technology, the total cost including post-treatments is becoming closer to the cost of the acid saccharification method. However, because the price of enzymes which accounts for a high proportion of the total cost of the enzymatic saccharification method is still high, in order to achieve practical application of the enzymatic saccharification method, a further decrease in the cost of the enzymes is important.

As a technology for decreasing the cost of the enzymatic saccharification method, the development of a method for a pretreatment that facilitates the access of an enzyme to cellulose fibers, or the development of a method of efficiently saccharifying crystalline cellulose, and the development of a method for efficient recovery and reuse of enzymes can be considered.

A lignocellulose material from which lignin has not been removed is not easily degraded by enzymes as compared with a lignocellulose material from which lignin has been removed, and is not saccharified so that the lignocellulose material from which lignin has not been removed remains as a residue in the saccharification liquid together with impurities such as resins and metals. In general, this residue is separated by screening, centrifugation or the like and is discarded. Since this residue contains a large amount of adsorbed enzymes, which occupy a large proportion of the cost in the enzymatic saccharification method, there is a problem that if the residue separated from the reaction liquid is directly discarded, the highly expensive enzymes are also discarded. That is, it is desired to recover and effectively utilize the residue for the purpose of reducing the cost of the enzymatic saccharification method. In regard to the technology of reusing the residue recovered in the enzymatic saccharification method, there have been reports on a method of combusting the residue and obtaining heat energy (PTL 5), a method of subjecting the residue to hydrothermal gasification, and synthesizing ethanol from the produced synthesis gas using an ethanol synthesis catalyst (PTL 6), a method of utilizing the residue as a fuel or a fertilizer (PTL 7), and a method of utilizing the residue as heat energy (PTL 8). However, since these methods cause large increases in the cost as a result of the addition of treatment processes, in the case of designing a practically useful facility, it cannot be said that these methods are satisfactory as methods for addressing the problem of cost reduction.

As means for recovering enzymes in the residue such as described above, washing of the residue can be taken into consideration. However, since the enzymes are firmly bound to cellulose through the cellulose binding domain (CBD) that specifically adsorbs to cellulose, which is carried by the enzymes in the molecules, it has been difficult to sufficiently recover the enzymes that have been adsorbed to cellulose, by simple water washing.

Thus, for the purpose of improving the recovery ratio of enzymes, a method of treating the enzymes by adding a surfactant (see PTL 1), and the like have been suggested. However, even in the surfactant treatment method, it cannot be said that the recovery ratio of enzymes is satisfactory, and the method is not practical from the viewpoint that there is a concern for the deactivation of enzymes due to the addition of chemicals, an increase in the cost as a result of the addition of treatment processes, and the adverse effects on microorganisms in the fermentation step that follows.

As the method of recovering enzymes from a saccharide solution, a method of using ultrafiltration (see PTL 2), a method of adsorbing and recovering enzymes by adding cellulose again to the saccharide solution (see PTL 3), and the like have been suggested. However, the ultrafiltration method has a problem that fine impurities clog the filtration membrane, and thus a sufficient treatment speed and a sufficient enzyme recovery ratio cannot be obtained, and it is difficult to achieve sufficient enzyme recovery with the method of recovering by cellulose addition.

A method of reusing a lignocellulose residue to which enzymes are adsorbed, in the subsequent batch of enzymatic saccharification, without going through a step of detaching the adsorbed enzymes has been suggested (PTL 4).

In this method, since the accumulation of the residue cannot be avoided, there is a concern for a decrease in the reaction efficiency. Furthermore, in connection with enzymes having the CBD, such as CBH (cellobiohydrases), recycling of enzymes can be achieved by re-treating the lignocellulose residue in the subsequent batch; however, since there are occasions in which β-glucosidases and the like are liberated in the supernatant, it is difficult to recycle all of the cellulases that have been added.

Also, in this method, because the undegraded residue itself is in a state of being not easily degradable even if mixed again with an enzyme solution, it is desired to bring the undegraded residue to a state of being easily saccharifiable. The inventors of the present invention found that when an undegraded residue recovered by solid-liquid separation is mechanically treated and is subjected to saccharification and fermentation again, the ethanol output is increased (PTL 9). However, this method has a problem that the residue that has been used as a raw material is a residue recovered by using a 420-mesh (38-μm) screen and includes fibers of a wide range of sizes. Fibers of large sizes with a large amount of adsorbed lignin are not easily degraded by enzymes, and are therefore not sufficiently saccharified if not subjected to a pretreatment (mechanical treatment or the like). If only those fibers of small sizes with a small amount of adsorbed lignin could be selectively recovered and enzymatically saccharified again as a raw material without being subjected to a pretreatment, an enhancement of the ethanol output with high efficiency could be expected.

As a method of decreasing the cost of enzymes, methods of recycling enzymes have been reported. According to the method of Scott, C. D. and colleagues (Non-PTL 1), a continuous system is contemplated, which is provided with a recycle line having a grinding apparatus based on a high speed centrifugal pump which, in a main reaction tank which enzymatically hydrolyzes an old paper raw material by adding a large amount of an enzyme (80 to 160 units relative to 1 g of a substrate in terms of filter paper degradation activity), removes produced glucose and cellobiose components with high shear force on the surface of unreacted old paper in the enzymatic hydrolysate, and thereby always exposes new cellulose fiber surfaces; a membrane separation apparatus which separates the unreacted raw material and the hydrolysate from the treatment liquid coming from the grinding apparatus, and circulates only the unreacted raw material to the main reaction tank; and a filtering apparatus which separates enzymes and produced glucose and cellobiose from the hydrolysate coming from the membrane separation apparatus, and circulates only the enzymes to the main reaction tank, and the cost is predicted. According to this system, the saccharification ratio is 100% in 25 hours, and the residual ratio of enzymes is 95% or higher in 24 hours. Also, it is described that enzymes adsorb to the residue and are eliminated, that the adsorptive function of enzymes to the residue may be decreased by increasing the pH to 5 to 7, and it is reported that the adsorptive function of enzymes can be decreased by lowering the temperature to 5° C.

As a method of recovering and reusing the enzymes, a method has been reported in which birch wood that has been steam blasting treated is added to a saccharification tank at a concentration of 5%, 20,000 units of a cellulase is added thereto, a saccharide solution and an enzyme solution are separated by ultrafiltration, and while the enzyme is recovered and reused, 630 g of monosaccharides are obtained from 2 kg of birch wood over 8 days. It is considered that the amount of the enzyme used could be saved by 20% by this method (Non-PTL 2).

CITATION LIST

Patent Literature

[PTL 1] JP-A-63-87994
[PTL 2] JP-A-61-234790
[PTL 3] JP-A-55-144885
[PTL 4] JP-A-2010-98951
[PTL 5] Japanese Patent No. 4447148
[PTL 6] JP-A-2005-168335
[PTL 7] JP-A-2008-54676
[PTL 8] JP-A-2009-106932
[PTL 9] Japanese Patent Application No. 2009-190862

Non-Patent Literature

[NPL 1] Scott, C. D., Rothrock, D. S., Appl. Biochem. Biotechnol., 45/46, pp. 641-653 (1994)
[NPL 2] Ishihara, M., et al., Biotechnol. Bioeng., 37, 948-954 (1991)

SUMMARY OF INVENTION

Technical Problem

The technology of producing saccharides from a biomass of lignocellulose and the like is a technology capable of newly supplying fuels or plastic raw materials that have been hitherto dependent on fossil resources, and is a technology that is particularly helpful to the establishment of a recycling-oriented society. As described above, various technologies have been developed hitherto, but it is a problem that the technology is not economical, primarily because of the high cost of the enzymes needed in saccharification.

As described above, there have been various attempts to reduce the amount of enzymes used by recovering and repeatedly using the enzymes used in saccharification. However, because enzymes strongly adsorb to the residue generated at the time of saccharification, the recovery ratio is decreased, and the problem could not be solved. As such, the strong adsorption of enzymes to the residue generated at the time of enzymatic saccharification is the biggest problem at the time of enzyme recovery, and if this can be solved, the recyclability of the enzymes can be improved, the cost can be reduced, and the economic efficiency of the enzymatic saccharification treatment method can be greatly improved. Therefore, it is an object of the present invention to provide a method that can effectively utilize, without wasting, the enzymes introduced for the enzymatic saccharification treatment of a lignocellulose material, and to provide a method for producing ethanol with high ethanol yield in the ethanol production process using lignocellulose as a raw material.

Solution to Problem

In order to address the problems described above, the inventors of the present invention conducted an investigation on the method of decreasing the cost, in regard to a process of continuously carrying out an enzymatic saccharification reaction, by repeatedly using, with an increased recovery ratio, an enzyme that is expensive and accounts for a very large proportion of the total cost, and as a result, the inventors achieved the following invention. The present invention is based on the idea that employing means for suppressing the adsorption of enzymes to the lignocellulose raw material or the reaction residue in an enzymatic saccharification reaction liquid, is means for facilitating the separation of enzymes from the reaction liquid after the enzymatic saccharification reaction is facilitated, and also for preventing the discharge of the enzymes out of the system together with the residue that is discarded. Also, the inventors found that when only the fine fibers that are easily saccharified from the residue included in the culture fluid of a parallel saccharifying fermentation process are recovered, and saccharification or parallel saccharifying fermentation is carried out using the recovered fine fibers as a raw material, the ethanol output is enhanced, and the amount of residue discharged in the process is reduced. Thus, the inventors completed the present invention as described below.

The present invention is based on the findings described above, and includes the following embodiments.

(1) A method for the enzymatic saccharification treatment of a lignocellulose-based raw material, the method including adding a lignocellulose-based raw material which has been subjected to a pretreatment for making the raw material appropriate for an enzymatic saccharification reaction, together with an electrolyte containing a water-soluble salt, to cellulose saccharification enzyme-containing water; subjecting the lignocellulose-based raw material as a raw material suspension whose electrical conductivity has been adjusted to 5 mS/cm to 25 mS/cm, to an enzymatic saccharification treatment through an enzymatic saccharification reaction; separating and recovering the reaction product and an enzyme-containing solution from the treated suspension after the enzymatic saccharification treatment; and recycling the recovered enzyme-containing solution as an enzyme for the enzymatic saccharification treatment process.

(2) The method for the enzymatic saccharification treatment of a lignocellulose-based raw material as described in (1), wherein the pretreatment for making the raw material appropriate for an enzymatic saccharification reaction is a pretreatment including a chemical treatment of immersing the lignocellulose-based raw material in a solution containing an alkali chemical selected from sodium hydroxide, potassium hydroxide, calcium hydroxide, sodium carbonate and sodium hydrogen carbonate, or a mixture thereof, or a mixture of sodium sulfite and such an alkali.

(3) The method for the enzymatic saccharification treatment of a lignocellulose-based raw material as described in (1) or (2), wherein the lignocellulose-based raw material is forest residues.

(4) The method for the enzymatic saccharification treatment of a lignocellulose-based raw material as described in (1) or (2), wherein the lignocellulose-based raw material is tree bark.

(5) The method for the enzymatic saccharification treatment of a lignocellulose-based raw material as described in any one of (1) to (4), wherein the water-soluble salt is at least one water-soluble salt selected from alkali metal salts and alkaline earth metal salts.

(6) The method for the enzymatic saccharification treatment of a lignocellulose-based raw material as described in any one of (1) to (5), wherein the water-soluble salt is a salt selected from the group consisting of halides, sulfates, sulfites, thiosulfates, carbonates, hydrogen carbonates, phosphates, dihydrogen phosphates, hydrogen diphosphates, acetates, and citrates of alkali metals and alkaline earth metals.

(7) The method for the enzymatic saccharification treatment of a lignocellulose-based raw material as described in any one of (1) to (6), wherein the enzymatic saccharification treatment method is a method of subjecting a lignocellulose-based raw material to an enzymatic saccharification treatment according to a series of processes including a pretreatment step of subjecting a lignocellulose-based raw material to a treatment for making the lignocellulose-based raw material appropriate for an enzymatic saccharification reaction; an enzymatic saccharification treatment step of adding the pretreated lignocellulose-based raw material, together with an electrolyte containing a water-soluble salt, to cellulose saccharification enzyme-containing water, and treating the lignocellulose-based raw material as a raw material suspension whose electrical conductivity has been adjusted to 5 mS/cm to 25 mS/cm, through an enzymatic saccharification reaction; a solid-liquid separation step of removing a solid residue from the treated suspension coming from the enzymatic saccharification treatment step; a centrifugation step of centrifuging the liquid fraction coming from the solid-liquid separation step, and thereby obtaining a liquid fraction which contains enzymes and saccharides and has all the remaining residue removed; a membrane separation step of separating the liquid fraction coming from the centrifugation step into an enzyme-containing solution and a produced saccharide-containing solution; and an enzyme recycling step of recycling and supplying the enzyme-containing solution obtainable from the membrane separation step to the enzyme saccharification treatment step as an enzyme source.

(8) The method for the enzymatic saccharification treatment of a lignocellulose-based raw material as described in any one of (1) to (7), wherein the enzymatic saccharification treatment step is a parallel saccharifying fermentation treatment step of carrying out a treatment based on an enzymatic saccharification reaction of a lignocellulose-based raw material and a fermentation treatment of produced saccharides by a microorganism for fermentation in combination by using a cellulase preparation and a microorganism for fermentation which uses saccharides as a fermentation substrate (=raw material) in combination, and thereby producing a fermentation product together with saccharides.

(9) The method for the enzymatic saccharification treatment of a lignocellulose-based raw material as described in (8), wherein the enzymatic saccharification method is a method of subjecting a lignocellulose-based raw material to a parallel saccharifying fermentation treatment according to a series of processes including a pretreatment step of subjecting a lignocellulose-based raw material to a treatment for making the lignocellulose-based raw material appropriate for an enzymatic saccharification reaction; a parallel saccharifying fermentation treatment step of adding the pretreated lignocellulose-based raw material, together with a microorganism for fermentation which uses saccharides as a fermentation substrate, and with an electrolyte containing a water-soluble salt, to cellulose saccharification enzyme-containing water, and subjecting the lignocellulose-based raw material as a raw material suspension whose electrical conductivity has been adjusted to 5 mS/cm to 25 mS/cm, to both an enzymatic saccharification treatment and a fermentation treatment of using the produced saccharides as a substrate; a solid-liquid separation step of removing a solid residue from the treated suspension coming from the enzymatic saccharification treatment step; a distillation step of separating and recovering the fermentation product from the liquid fraction coming from the solid-liquid separation step through distillation; a centrifugation step of centrifuging the residual distillate coming from the distillation step to remove any remaining residue, and thereby obtaining a liquid fraction containing enzymes and saccharides; a membrane separation step of separating the liquid fraction coming from the centrifugation step into an enzyme-containing solution and a saccharide-containing solution; and an enzyme recycling step of recycling and supplying the enzyme-containing solution obtainable from the membrane separation step to the enzyme saccharification treatment step as an enzyme source.

(10) The method for the enzymatic saccharification treatment of a lignocellulose-based raw material as described in (9), wherein the saccharide-containing solution separated and recovered from the membrane separation step is a liquid containing saccharides which includes oligosaccharides as main components.

(11) The method for the enzymatic saccharification treatment of a lignocellulose-based raw material as described in (9), wherein the liquid fraction coming from the centrifugation step is recycled and supplied to the enzyme saccharification treatment step as an enzyme-containing solution containing saccharides, without going through the membrane separation step.

(12) The method for the enzymatic saccharification treatment of a lignocellulose-based raw material as described in (8), wherein the enzymatic saccharification treatment method is a method of subjecting a lignocellulose-based raw material to a parallel saccharifying fermentation treatment according to a series of processes including a pretreatment step of subjecting a lignocellulose-based raw material to a treatment for making the lignocellulose-based raw material appropriate for an enzymatic saccharification reaction; a parallel saccharifying fermentation treatment step of adding the pretreated lignocellulose-based raw material, together with a microorganism for fermentation which uses saccharides as a fermentation substrate, and with an electrolyte containing a water-soluble salt, to cellulose saccharification enzyme-containing water, and subjecting the lignocellulose-based raw material as a raw material suspension whose electrical conductivity has been adjusted to 5 mS/cm to 25 mS/cm, to both an enzymatic saccharification treatment of treating the lignocellulose-based raw material through an enzymatic saccharification reaction and a fermentation treatment of using the produced saccharides as a substrate; a solid-liquid separation step of separating the treated suspension coming from the parallel saccharifying fermentation treatment step into a residue and a liquid fraction using a screw press having a screen size of 1.0 mm to 2.0 mm; a sieve treatment step of separating the liquid fraction coming from the solid-liquid separation step into fine fibers and a liquid fraction through a sieve treatment using a 80- to 600-mesh sieve; a distillation step of separating and recovering a fermentation product from the liquid fraction obtained after the sieve treatment by excluding fine fibers, through distillation; a centrifugation step of centrifuging the residual distillate coming from the distillation step to remove any remaining residue, and thereby obtaining a liquid fraction containing enzymes and saccharides; and a step of recycling and supplying the liquid fraction coming from the centrifugation step to the enzyme saccharification treatment step as an enzyme-containing solution containing saccharides, without going through the membrane separation step.

Advantageous Effects of Invention

According to the enzymatic saccharification treatment method of the present invention, there is provided a method for the continuous enzymatic saccharification treatment of a lignocellulose-based biomass, which has a very small enzyme loss and high economic efficiency, as a result of suppressed adsorption of saccharification enzymes to an unreacted portion or a reaction residue of the lignocellulose-based raw material, and facilitated separation and recovery of saccharification enzymes from the enzyme-treated suspension.

Furthermore, according to the present invention, the ethanol output can be increased by selectively recovering fine fibers included in the culture fluid obtained after parallel saccharifying fermentation using lignocellulose as a raw material, and subjecting the recovered fine fibers as a raw material to saccharification or parallel saccharifying fermentation again.

DESCRIPTION OF EMBODIMENTS

Figure 1:
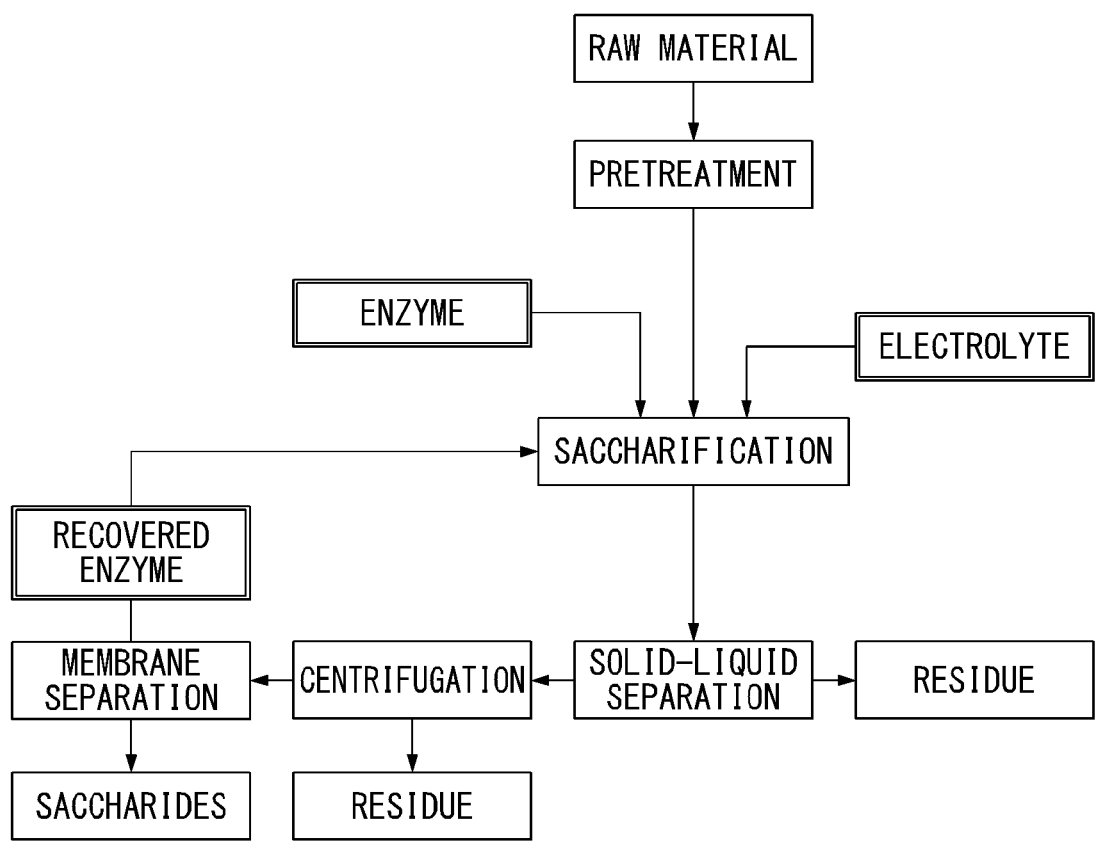
FIG. 1 is a process flow diagram showing an embodiment of the method for the enzymatic saccharification treatment of a lignocellulose-based raw material of the present invention.

Hereinafter, the present invention will be described in more detail.

<Lignocellulose-Based Raw Material>

Examples of the lignocellulose-based raw material used as the raw material for the method of the present invention include, as ligneous materials, chips or bark of timber for paper production, forest residues, timber from forest thinning, and the like; sawdust generated from sawmills and the like; pruned branches and leaves, and construction waste materials. Examples of herbaceous materials include agricultural wastes such as kenaf, rice straw, wheat straw and bagasse; residues and wastes of industrial crops such as oil crops and rubber (for example, EFB: Empty Fruit Bunch); and lignocellulose-based biomasses of herbaceous energy crops such as such as Erianthus, Miscanthus, and Napier grass. Furthermore, as the lignocellulose-based raw material according to the present invention, paper originating from wood, old paper, pulp, pulp sludge, and the like can also be used.

Among the ligneous lignocellulose-based raw materials described above, tree bark is substantially of effective use at the present, large amounts of bark having uniform quality is available from sawmills or chip mills, and soft and soluble components are present in large proportions in the trunk part of wood. Thus, bark is particularly preferable as a raw material for a saccharification treatment or a parallel saccharifying fermentation treatment.

For example, the bark of trees that belong to the genus *Eucalyptus* or the genus *Acacia*, which are generally used for papermaking raw materials, are available in large quantities in a stable manner from sawmills or chip mills for papermaking raw materials, and therefore, tree bark is particularly suitably used.

<Pretreatment for Making Raw Material Appropriate for Enzymatic Saccharification Treatment>

The pretreatment for making a raw material appropriate for the enzymatic saccharification treatment of the present invention is a treatment by which the following pretreatment is carried out on the lignocellulose-based raw material as described above, and thereby lignocellulose is brought to a state of being enzymatically saccharifiable:

a chemical treatment, a hydrothermal treatment, a pressurized hot water treatment, a hydrothermal treatment with added carbon dioxide, a steam treatment, mechanical treatments such as a wet crushing treatment, a mechanical grinding treatment, and a shredded fiber-forming treatment, a dilute sulfuric acid treatment, a steam blasting treatment, an ammonia blasting treatment, a carbon dioxide blasting treatment, an ultrasonic irradiation treatment, a microwave irradiation treatment, an electron beam irradiation treatment, a γ-ray irradiation treatment, a supercritical treatment, a subcritical treatment, an organic solvent treatment, a phase separation treatment, a wood rotting fungus treatment, a green solvent activation treatment, various catalyst treatments, a radical reaction treatment, and an ozone oxidation treatment.

These treatments may be carried out singly or in combinations of plural treatments.

Among them, it is preferable to subject the lignocellulose-based biomass to one or more pretreatments selected from a chemical treatment, a pressurized hot water treatment, a shredded fiber-forming treatment, and a mechanical grinding treatment.

The chemical treatment is a treatment of immersing a lignocellulose-based raw material in an aqueous solution of a chemical such as an acid or an alkali, and thereby bringing the lignocellulose-based raw material to a state appropriate for the enzymatic saccharification treatment of the subsequent step.

The chemical and the like used in the chemical treatment are not particularly limited, but for example, one or more are selected from hydroxides, sulfides such as sulfuric acid and dilute sulfuric acid, carbonates, sulfates and sulfites of alkali metals and alkaline earth metals. An alkali treatment achieved by immersing the lignocellulose-based raw material in an aqueous solution of one or more chemicals selected from sodium hydroxide, calcium hydroxide, sodium sulfide, sodium carbonate, calcium carbonate and sodium sulfite, is suitable as a chemical treatment. Furthermore, a chemical treatment based on an oxidizing agent such as ozone or chlorine dioxide can also be carried out.

It is suitable to carry out the chemical treatment in combination with a mechanical treatment such as a shredded fiber-forming treatment or a mechanical grinding treatment as described above, as a post-treatment of those pretreatments.

The amount of the chemical added to be used in the chemical treatment can be arbitrarily adjusted according to the circumstances, but from the viewpoint of chemical cost reduction, and from the viewpoint of preventing a decrease in the yield due to elution and over-degradation of cellulose, the amount is preferably 50 parts by mass or less based on 100 parts by mass of dry lignocellulose-based raw material. The immersion time in the aqueous solution of a chemical and the treatment temperature in the chemical treatment can be arbitrarily set in accordance with the raw material or chemical used, but generally, the chemical treatment can be carried out for a treatment time of 20 to 90 minutes and at a treatment temperature of 80° C. to 200° C. Since elution into the liquid side or over-degradation of cellulose may occur when severe treatment conditions are applied, it is preferable to set the treatment time to 70 minutes or less and the treatment temperature to 180° C. or lower. More preferably, the treatment time is 30 minutes to 1 hour, and the treatment temperature is 80° C. to 130° C.

As the mechanical treatment, any mechanical means such as shredding, cutting and grinding may be used, and lignocellulose is thereby made prone to be saccharified by the saccharification fermentation treatment process of the subsequent step. There are no particular limitations on the machine apparatus used, but for example, a single-screw shredder, a twin-screw shredder, a hammer crusher, a refiner, and a kneader can be used.

For a lignocellulose-based raw material which has been subjected to a pretreatment for making the raw material appropriate for the treatment based on an enzymatic saccharification reaction, it is preferable to carry out a disinfection treatment before the lignocellulose-based raw material in the preparation of a lignocellulose-based raw material suspension. If unwanted bacteria are incorporated into the lignocellulose-based biomass raw material, there occurs a problem that the unwanted bacteria consume saccharides when saccharification by enzymes is carried out, and the yield of the product is decreased.

The disinfection treatment may be carried out by a method of exposing the raw material to a pH at which the growth of bacteria is difficult, such as an acidic pH or an alkaline pH, but may also be carried out by a method of treating the raw material under a high temperature, or both of the methods may be combined. For the raw material after an acid or alkali treatment, it is preferable to adjust the treated raw material to a neutral pH, or to a pH appropriate for a saccharification treatment or a saccharification fermentation treatment, and then to use it as a raw material. Also, even in the case of performing high temperature disinfection, it is preferable to cool the treated raw material to room temperature or to a temperature appropriate for the treatment in the saccharification fermentation process, and then to use it as a raw material. As such, when the raw material is sent out after the temperature or pH is adjusted, the enzymes can be prevented from being exposed to a pH or a temperature other than a suitable pH or a suitable temperature, and being deactivated.

The lignocellulose-based raw material that has been subjected to a pretreatment for making the raw material appropriate for the treatment based on an enzymatic saccharification reaction, is further mixed with an appropriate amount of water, an enzyme, and a water-soluble salt, and optionally with a microorganism needed for fermentation, such as a yeast, and thus a raw material suspension is prepared. The raw material suspension is supplied to the enzymatic saccharification treatment step after the electrical conductivity is adjusted to a predetermined value. A representative process for carrying out the enzymatic saccharification treatment method is shown in FIG. 1.

<Enzymatic Saccharification Treatment>

In the case of the enzymatic saccharification treatment method according to the process of FIG. 1, in the enzymatic saccharification treatment step indicated as "Saccharification" in FIG. 1, a raw material suspension that has been prepared by adding the lignocellulose-based raw material supplied from the pretreatment step indicated as "Pretreatment", a saccharification enzyme, and a water-soluble salt as an electrolyte to an appropriate amount of water, is subjected to enzymatic saccharification under stirring. The concentration of the lignocellulose raw material in the raw material suspension is preferably 1 mass % to 30 mass %. If the concentration is less than 1 mass %, the final concentration of the product is too low, and there occurs a problem that the cost for the concentration of the product increases. Also, when the concentration is greater than 30 mass % and the raw material is highly concentrated, stirring of the raw material becomes difficult, and there occurs a problem that productivity is lowered.

The electrical conductivity of the raw material suspension in the enzymatic saccharification treatment step is preferably maintained in the range of 5 mS/cm to 25 mS/cm.

The pH is selected in the range of 3.5 to 10.0, in which the enzyme used is not likely to be deactivated, but it is more preferable to maintain the pH in the range of 3.5 to 7.5.

The pH at the saccharification step or the parallel saccharifying fermentation step is preferably maintained in the range of 3.5 to 10.0, and more preferably in the range of 4.0 to 7.5.

The temperature for the enzymatic saccharification treatment is not particularly limited as long as the temperature is in the range of the optimal temperature of the enzyme, and the temperature is generally 25° C. to 50° C., and preferably 30° C. to 40° C.

Furthermore, the mode of the enzymatic saccharification reaction is preferably a continuous mode, but a semi-batch mode or a batch mode may also be used.

The reaction time may vary with the enzyme concentration, but in the case of a batch mode, the reaction time is generally 10 to 240 hours, and preferably 15 to 160 hours. Also in the case of a continuous mode, the general average retention time is 10 to 150 hours, and preferably 15 to 100 hours.

The cellulolytic enzyme used in the enzymatic saccharification treatment or the parallel saccharifying fermentation is appropriately selected from a group of enzymes that are collectively referred to as so-called cellulases, which have cellobiohydrolase activity, endoglucanase activity, and beta-glucosidase activity.

In regard to the various cellulolytic enzymes, enzymes having the respective activities may be added in an appropriate amount; however, since many of those commercially available cellulase preparations have the various cellulase activities described above as well as hemicellulase activity, commercially available cellulase preparations may also be used.

Examples of the commercially available cellulase preparations include cellulase preparations originating from the genus *Trichoderma*, the genus *Acrremonium*, the genus *Aspergillus*, the genus *Phanerochaete*, the genus *Trametes*, the genus *Humicola*, and the genus *Bacillus*. Examples of commercial products of such cellulase preparations include Cellucine T2 (manufactured by HPI Co., Ltd.), Meicelase (manufactured by Meiji Seika Kaisha, Ltd.), Novozyme 188 (manufactured by Novozymes A/S), Multifect CX10L (manufactured by Genencor International, Inc.), and GC220 (manufactured by Genencor International, Inc.) (all trade names).

The amount of the cellulase preparation used based on 100 parts by mass of the raw material solids content is preferably 0.5 to 100 parts by mass, and particularly preferably 1 to 50 parts by mass.

As the water-soluble salt that is added as an electrolyte, those selected from acidic salts, basic salts, neutral salts, and salt-containing buffer solutions such as an acetate buffer solution and a citrate buffer solution can be used singly or in combination. The concentration of the water-soluble salt can be freely set in a range that does not have adverse effects on the enzymatic saccharification reaction.

Among them, a water-soluble salt selected from alkali metal salts and alkaline earth metal salts is preferable. Examples of the alkali metal salts and alkaline earth metal salts include water-soluble salts selected from the group consisting of halides, sulfates, sulfites, thiosulfates, carbonates, hydrogen carbonates, phosphates, dihydrogen phosphates, hydrogen diphosphates, acetates, and citrates of alkali metals and alkaline earth metals.

In the present invention, a water-soluble salt can be added as an electrolyte in the enzymatic saccharification treatment process.

In the enzymatic saccharification treatment process, it is preferable to add an electrolyte to the raw material suspension and to maintain the electrical conductivity of the raw material suspension in the range of 5 mS/cm to 25 mS/cm. When the electrical conductivity is maintained in the range of 5 mS/cm to 25 mS/cm, the adsorption of enzymes to the unreacted components or the reaction residue of the lignocellulose raw material, and therefore, the recycling ratio of the enzymes in the enzymatic saccharification treatment process can be maintained at a high level over a long time period. The electrolyte can be added without any limitation in any step, as long as the step is in the enzymatic saccharification treatment process, and the step allows the operation of adding the electrolyte. It is preferable to add the electrolyte during the primary saccharification fermentation step because the operation is easy.

<Solid-Liquid Separation>

The treatment suspension discharged from the "saccharification step" is sent to the solid-liquid separation process having a filtration apparatus indicated as "Solid-liquid separation" in FIG. 1, and a solid residue is eliminated. The solid residue separated by the filtration apparatus in the solid-liquid separation process includes lignin, hemicellulose and cellulose. However, cellulose exists in a state of being protected by lignin and the like, and in a state in which further saccharification cannot be promoted, and therefore, cellulose is usually discharged out of the process.

Furthermore, the culture fluid discharged from the primary parallel saccharifying fermentation step is conveyed to the solid-liquid separation step and is separated into a liquid fraction (filtrate) and a residue (primary residue). As the apparatus for performing the solid-liquid separation, a screw press having a screen size of 1.0 mm to 2.0 mm is used. The screw press is an apparatus which does not easily undergo clogging caused by fibers due to the structure and is capable of efficiently performing solid-liquid separation with a relatively smaller amount of energy. In order to enhance the solid-liquid separation efficiency, back pressure may be applied.

The residue separated in the solid-liquid separation step includes lignin, hemicellulose and cellulose, and cellulose has lignin and the like adsorbed thereto and is thus in a state in which saccharification by enzymes is difficult. The residue obtained after the solid-liquid separation step includes a large amount of fibrous components that have not been degraded in the primary parallel saccharifying fermentation step, so that when the residue is subjected to a mechanical treatment or a chemical treatment, saccharification is facilitated (PTL 6).

The filtrate (liquid fraction) separated in the solid-liquid separation step is conveyed to the subsequent sieve treatment step.

<Centrifugation Step>

The liquid fraction from which a solid residue has been excluded in the solid-liquid separation step is subsequently sent to the centrifugation step indicated as "Centrifugation", and the remaining residue present in the liquid fraction coming from the solid separation step is removed. The liquid fraction is sent to the process for recovering a saccharide solution and an enzyme solution, which is indicated as "Membrane separation" in FIG. 1.

Figure 3:
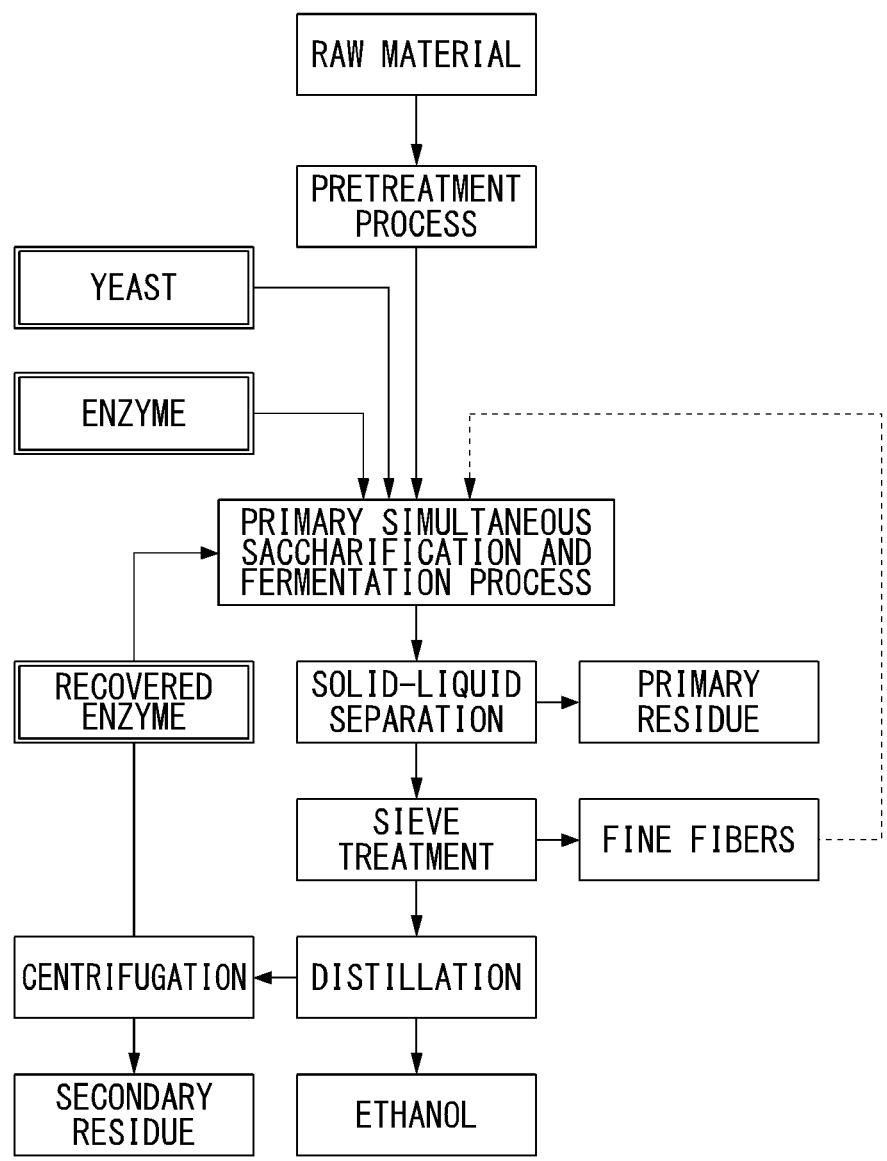
FIG. 3 is a diagram showing the production process flow of Example B1.

Furthermore, the residual distillate is conveyed to the centrifugation step, where the residue remaining therein (secondary residue) is removed by centrifugation, and then the liquid fraction is recycled to the primary parallel saccharifying fermentation process (see FIG. 3). This liquid fraction contains enzymes, and the enzymes are reused in the primary parallel saccharifying fermentation step. Meanwhile, the residue contains lignin, so that the residue can be recovered as a fuel for combustion and can be used as energy, or lignin can be recovered and effectively used.

<Membrane Separation Step>

The liquid fraction from which the remaining residue has been excluded in the centrifugation step is a liquid fraction containing enzymes and produced saccharides, and the liquid fraction is separated into an enzyme-containing solution and a saccharide-containing solution in the membrane separation step indicated as "Membrane separation" in FIG. 1 and is sent to an enzyme solution storage tank indicated as "Recovered enzyme", where the enzyme-containing solution is recycled as an enzyme source. The saccharide-containing solution is taken out directly as a product.

Since the saccharide-containing solution contains monosaccharides such as hexoses and pentoses, as well as oligosaccharides, if it is intended to produce monosaccharides, oligosaccharides may be separated and supplied to the "Saccharification step", so that the oligosaccharides can be further enzymatically treated and degraded into monosaccharides.

<Primary Parallel Saccharifying Fermentation Treatment Step>

The enzymatic saccharification treatment step indicated as the "Saccharification step" in FIG. 1 can be carried out as a so-called parallel saccharifying fermentation treatment process which simultaneously carries out a fermentation treatment using a microorganism that uses the saccharides produced by the enzymatic saccharification reaction as a raw material (fermentation substrate). In this case, a microorganism for fermentation which uses the produced saccharides as a fermentation substrate (fermentation raw material) is added to the raw material suspension, together with the saccharification enzyme. A typical process for carrying out the parallel saccharifying fermentation treatment method is shown in FIG. 2.

Figure 2:
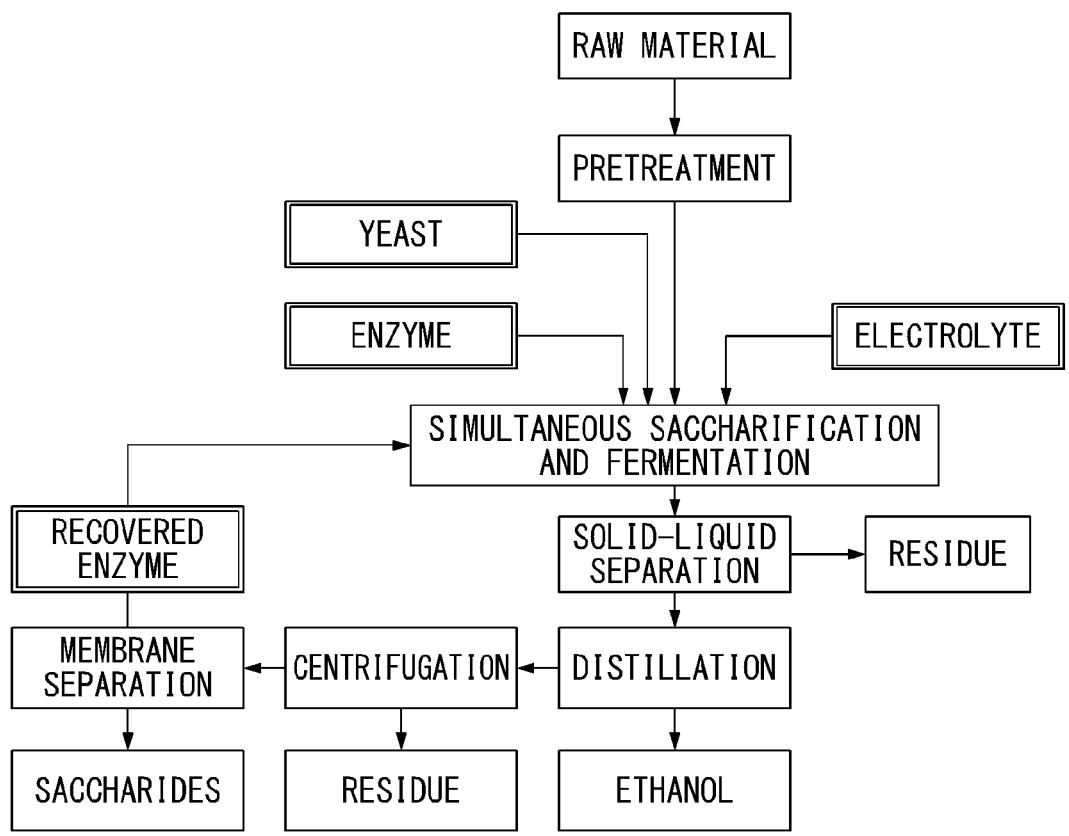
FIG. 2 is a process flow diagram showing the enzymatic saccharification treatment process of a lignocellulose-based raw material of the present invention, performed as a parallel saccharifying fermentation treatment process of performing an enzymatic saccharification treatment in combination with a fermentation treatment of using produced saccharides as a raw material.

In FIG. 2, the lignocellulose-based raw material that has been treated to a state appropriate for the enzymatic saccharification treatment in the pretreatment step is added to an appropriate amount of water together with a water-soluble salt as an electrolyte, a cellulolytic enzyme, and a microorganism for fermentation such as an alcohol yeast, and is subjected, in the form of a raw material suspension having the electrical conductivity adjusted to a predetermined value, to both a saccharification treatment of cellulose by an enzymatic saccharification reaction and a fermentation treatment such as alcohol fermentation using the produced saccharides as a fermentation substrate in the parallel saccharifying fermentation step.

The lignocellulose-based raw material that has been subjected to a pretreatment appropriate for saccharification fermentation is mixed with an appropriate amount of water, an enzyme, and a microorganism required for fermentation, such as a yeast, and the mixture is supplied to the primary parallel saccharifying fermentation step. A typical process of the parallel saccharifying fermentation treatment method is shown in FIG. 1.

In FIG. 3, the lignocellulose-based raw material that has been treated to a state appropriate for the saccharification fermentation treatment in the pretreatment step, is saccharified (cellulose→glucose) by enzymes and is subsequently fermented (glucose→ethanol) by a yeast.

As the microorganism used for fermentation, a yeast and the like are used. The microorganism may be added together with the medium and the like used in the culture thereof. As the yeast, well known yeasts that are described in PTL 3, for example, yeasts such as *Sacharomiyces cerevisae*, *Pichia stipitis*, *Issatchenkia orientalis*, *Candida brassicae*, and *Rhizopus javanicus* can be used.

The microorganism may be immobilized. If the microorganism is immobilized, the step of recovering the microorganism in the subsequent step can be omitted, or at least the burden posed by the recovery step can be reduced, and the risk of losing the microorganism can be reduced. Also, although it is not as advantageous as the immobilization of the microorganism, the recovery of the microorganism can be made easier by selecting a microorganism having a cohesive property.

In the processes of FIG. 2, the treated suspension discharged from the parallel saccharifying fermentation step is sent to the solid-liquid separation step where solids are removed from the suspension, and then the liquid fraction containing a fermentation product and saccharides is sent to the "Distillation step" indicated as "Distillation" in FIG. 2 in order to separate and recover the fermentation product. In the distillation step, the fermentation product is distilled and separated by a reduced pressure distillation apparatus. When reduced pressure distillation is used, the fermentation product can be separated at a low temperature, and therefore, deactivation of the enzymes can be prevented. As the reduced pressure distillation apparatus, a rotary evaporator, a flash evaporator and the like can be used.

The distillation temperature is preferably 25° C. to 60° C. If the distillation temperature is lower than 25° C., distillation of the product takes time, and productivity is decreased. Also, if the distillation temperature is higher than 60° C., the enzymes are thermally denatured and are deactivated, and the amount of enzymes to be newly added increases. Thus, the economic efficiency is deteriorated.

The concentration of the fermentation product remaining in the residual distillate after the distillation is preferably 0.1 mass % or less. When the fermentation product is adjusted to such a concentration, the amount of the fermentation product discharged together with the remaining residue in the centrifugation step in the downstream can be reduced, and the yield can be increased.

The residual distillate coming from the distillation step is subsequently sent to the centrifugation step indicated as "Centrifugation" in FIG. 2, and the remaining residue present in the residual distillate is excluded. Thus, a liquid fraction containing enzymes and saccharides is obtained.

This liquid fraction containing enzymes and saccharides is sent to the membrane separation step indicated as "Membrane separation" in FIG. 2, and is separated into an enzyme-containing solution and a saccharide-containing solution. The enzyme-containing solution is recycled and supplied to the "Parallel saccharifying fermentation step" via the enzyme solution storage tank indicated as "Recovered enzyme" in FIG. 2. Also, the saccharide-containing solution is collected in the saccharide solution storage tank indicated as "Saccharides" in FIG. 2 and is processed into saccharide products.

In the parallel saccharifying fermentation step, hexoses which are the enzymatic degradation products of cellulose, namely, glucose, mannose, galactose and the like, and pentoses originating from hemicellulose, namely, xylose and the like, as well as oligosaccharides are produced. Hexoses such as glucose are mainly used as the fermentation substrate, and alcohols such as ethanol are produced. Also, because pentoses and oligosaccharides are not used as fermentation substrates, pentoses and oligosaccharides are directly sent to the enzyme recovery step together with the enzymes. In this case, the pentoses may be added to the raw material suspension together with a yeast which certainly uses those pentoses as fermentation substrates, or may be subjected to a fermentation treatment in a separate process. Also, if necessary, the pentoses may be recovered as products.

Furthermore, the oligosaccharides may be recovered as products as necessary, or can be utilized as a raw material to be degraded to monosaccharides by enzymes in the parallel saccharifying fermentation step as discussed in the enzymatic saccharification treatment method according to the process of FIG. 1.

The suspension concentration of the lignocellulose-based raw material is preferably 1 mass % to 30 mass %. If the suspension concentration is less than 1 mass %, the final concentration of the product is too low, and there occurs a problem that the cost for the concentration of the product increases. Furthermore, if the concentration is greater than 30 mass % and the raw material is highly concentrated, stirring of the raw material becomes difficult, and there occurs a problem that productivity is lowered.

<Sieve Treatment Step>

The filtrate obtained after the solid-liquid separation is subjected to a sieve treatment, and is separated into fine fibers and a filtrate (liquid fraction). As the method of the sieve treatment, any sieve treatment apparatus capable of separating fine fibers can be used without particular limitations. As the sieve treatment apparatus, a screen, a filter press, and the like can be used. The mesh size of the sieve is preferably 80 mesh to 600 mesh (28 µm to 182 µm), and more preferably 150 mesh to 400 mesh (39 µm to 97 µm). In order to increase the treatment efficiency, a sieve vibrator may be attached, and vibration may be applied. The fine fibers separated by the treatment described above have a low lignin content as compared with the primary residue or the secondary residue, and can be easily saccharified by enzymes. Furthermore, when fine fibers are excluded by the sieve treatment, there is an advantage that the operation for a long time period of the apparatus that can reduce the amount of solids adhering to the reduced pressure distillation apparatus used in the distillation step in the downstream, is made possible. The recovered fine fibers may be conveyed to the primary saccharification fermentation step and may be used as the raw material for saccharification fermentation (see FIG. 3). Furthermore, the recovered fine fibers may be conveyed to a secondary saccharification fermentation step (a saccharification fermentation process different from the primary saccharification fermentation process) that will be described below and may be used as a raw material for the saccharification fermentation (see FIG. 4). Moreover, the recovered fine fibers may also be subjected to saccharification in a separate process. When the fine fibers are treated by saccharification or saccharification fermentation as such, the enzymes adsorbed to the fine fibers can be effectively utilized.

On the other hand, the filtrate separated by the sieve treatment is conveyed to the distillation step.

<Secondary Parallel Saccharifying Fermentation Treatment Step>

The secondary parallel saccharifying fermentation treatment step is a saccharification fermentation step independent from the primary parallel saccharifying fermentation treatment step, and saccharification fermentation may be carried out using fresh lignocellulose as a raw material, or saccharification fermentation may be carried out using the residue discharged during the process as a raw material. Furthermore, the saccharides that have not been fermented to ethanol in the primary parallel saccharifying fermentation step can also be fermented in the secondary parallel saccharifying fermentation treatment. In the primary parallel saccharifying fermentation step, hexoses originating from cellulose, namely, glucose, mannose, galactose and the like are fermented to ethanol, but xylose, which is a pentose originating from hemicellulose, may remain unreacted. In this case, a yeast which more certainly ferments pentoses may be added to the secondary parallel saccharifying fermentation treatment step, to ferment the pentoses. In the present invention, the fine fibers recovered by the sieve treatment can be conveyed to the secondary parallel saccharifying fermentation treatment step and can be treated by saccharification fermentation.

<Distillation Step>

Figure 4:
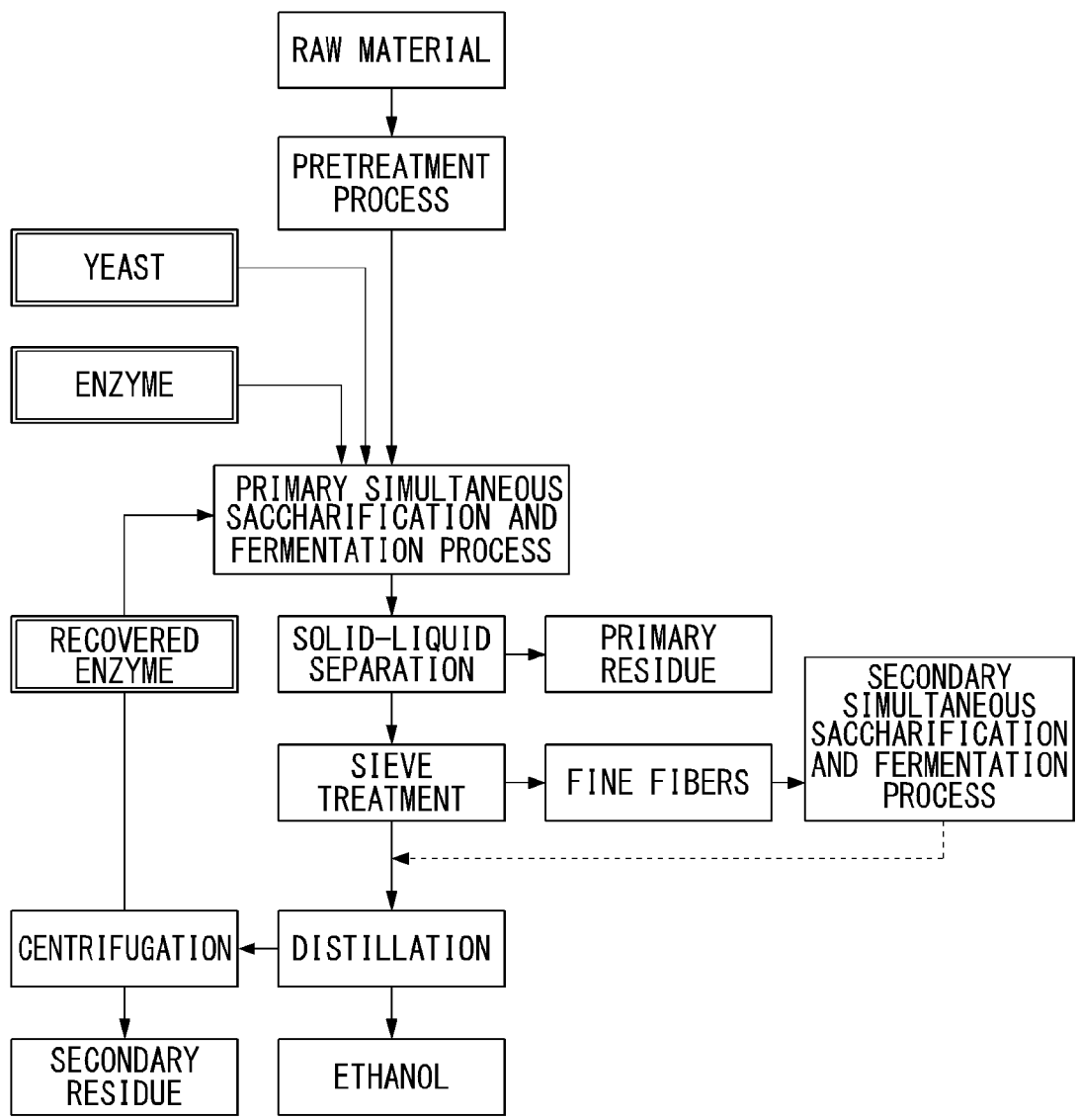
FIG. 4 is a diagram showing the production process flow of Example B2.

The filtrate obtained after the sieve treatment, or the treated liquid (culture fluid) obtained after the secondary parallel saccharifying fermentation treatment step is conveyed to the distillation step (see FIG. 3 and FIG. 4).

In the distillation step, the fermentation product is distilled and separated by a reduced pressure distillation apparatus. Since the fermentation product can be separated at a low temperature under reduced pressure, deactivation of the enzymes can be prevented. As the reduced pressure distillation apparatus, a rotary evaporator, a flash evaporator and the like can be used.

EXAMPLES

Hereinafter, the present invention will be described based on Examples, but the present invention is not intended to be limited by these Examples. In the respective Examples and Comparative Examples, the unit "%" indicates "mass %", and the unit "parts" indicates "parts by mass."

Example A1

100 g of crushed forest residues were introduced into 1000 ml of water containing 20 g of 48% caustic soda, and the forest residues were treated at 90° C. for 30 minutes. Subsequently, the mixture was ground with a refiner (clearance 0.5 mm). This product was dehydrated and washed with a screw press, and the resulting product was used as the substrate raw material.

The substrate raw material was added at a final concentration of 5%, CSL (corn steep liquor) was added at a final concentration of 1%, ammonium sulfate was added at a final concentration of 0.5%, and sodium chloride was added at a final concentration of 100 mM. Thus, 400 ml of a lignocellulose suspension having an electrical conductivity of 11.8 mS/cm was prepared.

The lignocellulose suspension prepared as described above was steam sterilized at 120° C. for 20 minutes and was cooled to 40° C. Subsequently, 10 ml of an enzyme (trade name: GC220; manufactured by Genencor International, Inc.) was added thereto.

A saccharification reaction was carried out at 30° C. and under stirring at 120 rpm, and 1 ml of the reaction liquid was collected after each of 24 hours and 48 hours and was centrifuged for 5 minutes at 10,000 rpm. The enzyme activity of the supernatant obtained thereby was measured.

The recovery ratio was calculated by using the activity of β-glucosidase, which is the most important in the enzyme recovery, as an index. The measurement of the activity was carried out by the method described below.

(β-Glucosidase Activity)

The measurement of the β-glucosidase activity was carried out by adding 4 μl of an enzyme solution to 16 μl of a 125 mM acetate buffer solution (pH 5.0) containing 1.25 mM 4-methyl-umberiferyl-glucoside, performing a reaction for 10 minutes at 37° C., subsequently adding 100 μl of a 500 mM glycine-NaOH buffer solution (pH 10.0) to terminate the reaction, and measuring the fluorescence intensity at 460 nm using an excitation light at 350 nm. The enzyme recovery ratio was determined by the following calculation formula.

Enzyme recovery ratio (%)=(Enzyme activity of supernatant/activity of added enzyme)×100

Example A2

The experiment was carried out in the same manner as in Example A1, except that instead of the sodium chloride added to a final concentration of 100 mM in the method of Example A1, sodium hydrogen carbonate was added to a final concentration of 100 mM. The electrical conductivity in the reaction system at this time was 8.6 mS/cm.

Example A3

100 g of crushed forest residues was introduced into 1000 ml of water containing 20 g of 48% caustic soda, and the forest residues were treated at 90° C. for 30 minutes. Subsequently, the mixture was ground with a refiner (clearance 0.5 mm). This product was dehydrated and washed with a screw press, and the resulting product was used as a substrate raw material.

The substrate raw material was added at a final concentration of 5%, CSL (corn steep liquor) was added at a final concentration of 1%, ammonium sulfate was added at a final concentration of 0.5%, and sodium chloride was added at a final concentration of 100 mM. Thus, 400 ml of a lignocellulose suspension having an electrical conductivity of 12.0 mS/cm was prepared.

The lignocellulose suspension prepared as described above was steam sterilized at 120° C. for 20 minutes and was cooled to 40° C. Subsequently, 10 ml of an enzyme (trade name: GC220; manufactured by Genencor International, Inc.) was added thereto.

Furthermore, a commercially available yeast (trade name: Maurivin: Mauri Yeast Australia Pty, Limited) was added to the raw material suspension prepared as described above, and the yeast was subjected to saccharification, fermentation and culture at 30° C. under stirring at 120 rpm, and 1 ml of the reaction liquid was collected after each of 24 hours and 48 hours and was centrifuged for 5 minutes at 10,000 rpm. The enzyme activity of the supernatant obtained thereby was measured.

Example A4

The experiment was carried out in the same manner as in Example A3, except that instead of the sodium chloride added to a final concentration of 100 mM in the method of Example A3, potassium chloride was added to a final concentration of 100 mM. The electrical conductivity in the reaction system at this time was 13.3 mS/cm.

Example A5

The experiment was carried out in the same manner as in Example A3, except that instead of the sodium chloride used in the method of Example A3 added to a final concentration of 100 mM, potassium iodide was added to a final concentration of 100 mM. The electrical conductivity in the reaction system at this time was 14.5 mS/cm.

Example A6

The experiment was carried out in the same manner as in Example A3, except that instead of the sodium chloride added to a final concentration of 100 mM in the method of Example A3, sodium sulfate was added to a final concentration of 100 mM. The electrical conductivity in the reaction system at this time was 14.7 mS/cm.

Example A7

The experiment was carried out in the same manner as in Example A3, except that instead of the sodium chloride added to a final concentration of 100 mM in the method of Example A3, sodium sulfite was added to a final concentration of 100 mM. The electrical conductivity in the reaction system at this time was 13.6 mS/cm.

Example A8

The experiment was carried out in the same manner as in Example A3, except that instead of the sodium chloride added to a final concentration of 100 mM in the method of Example A3, sodium thiosulfate was added to a final concentration of 100 mM. The electrical conductivity in the reaction system at this time was 16.9 mS/cm.

Example A9

The experiment was carried out in the same manner as in Example A3, except that instead of the sodium chloride added to a final concentration of 100 mM in the method of Example A3, sodium carbonate was added to a final concentration of 100 mM. The electrical conductivity in the reaction system at this time was 12.6 mS/cm.

Example A10

The experiment was carried out in the same manner as in Example A3, except that instead of the sodium chloride added to a final concentration of 100 mM in the method of Example A3, dipotassium hydrogen phosphate was added to a final concentration of 100 mM. The electrical conductivity in the reaction system at this time was 15.0 mS/cm.

Example A11

The experiment was carried out in the same manner as in Example A3, except that instead of the sodium chloride added to a final concentration of 100 mM in the method of Example A3, disodium hydrogen phosphate was added to a final concentration of 100 mM. The electrical conductivity in the reaction system at this time was 11.9 mS/cm.

Example A12

The experiment was carried out in the same manner as in Example A3, except that instead of the sodium chloride added to a final concentration of 100 mM in the method of Example A3, sodium hydrogen carbonate was added to a final concentration of 100 mM. The electrical conductivity in the reaction system at this time was 8.9 mS/cm.

Example A13

The experiment was carried out in the same manner as in Example A3, except that instead of the sodium chloride added to a final concentration of 100 mM in the method of Example A3, trisodium citrate was added to a final concentration of 100 mM. The electrical conductivity in the reaction system at this time was 15.4 mS/cm.

Example A14

The experiment was carried out in the same manner as in Example A3, except that instead of the sodium chloride added to a final concentration of 100 mM in the method of Example A3, an acetate buffer (pH 5.0) was added to a final concentration of 100 mM. The electrical conductivity in the reaction system at this time was 7.1 mS/cm.

Example A15

The experiment was carried out in the same manner as in Example A3, except that instead of the sodium chloride added to a final concentration of 100 mM in the method of Example A3, a citrate buffer (pH 5.0) was added to a final concentration of 100 mM. The electrical conductivity in the reaction system at this time was 10.9 mS/cm.

Example A16

100 g of crushed bark of *Eucalyptus globulus* was introduced into 1000 ml of water containing 20 g of 48% caustic soda, and the forest residues were treated at 90° C. for 30 minutes. Subsequently, the mixture was ground with a refiner (clearance 0.5 mm). This product was dehydrated and washed with a screw press, and the resulting product was used as a substrate raw material.

The substrate raw material was added at a final concentration of 5%, CSL (corn steep liquor) was added at a final concentration of 1%, ammonium sulfate was added at a final concentration of 0.5%, and sodium chloride was added at a final concentration of 100 mM. Thus, 400 ml of a lignocellulose suspension having an electrical conductivity of 11.8 mS/cm was prepared.

The lignocellulose suspension prepared as described above was steam sterilized at 120° C. for 20 minutes and was cooled to 40° C. Subsequently, 10 ml of an enzyme (trade name: GC220; manufactured by Genencor International, Inc.) was added thereto.

A saccharification reaction was carried out at 30° C. under stirring at 120 rpm, and 1 ml of the reaction liquid was collected after each of 24 hours and 48 hours and was centrifuged for 5 minutes at 10,000 rpm. The enzyme activity of the supernatant obtained thereby was measured.

Example A17

100 g of crushed bark of *Eucalyptus globulus* was introduced into 1000 ml of water containing 20 g of 48% caustic soda, and the crushed bark was treated at 90° C. for 30 minutes. Subsequently, the mixture was ground with a refiner (clearance 0.5 mm). This product was dehydrated and washed with a screw press, and the resulting product was used as a substrate raw material.

The substrate raw material was added at a final concentration of 5%, CSL (corn steep liquor) was added at a final concentration of 1%, ammonium sulfate was added at a final concentration of 0.5%, and sodium chloride was added at a final concentration of 100 mM. Thus, 400 ml of a lignocellulose suspension having an electrical conductivity of 11.8 mS/cm was prepared.

The lignocellulose suspension prepared as described above was steam sterilized at 120° C. for 20 minutes and was cooled to 40° C. Subsequently, 10 ml of an enzyme (trade name: GC220; manufactured by Genencor International, Inc.) was added thereto. Furthermore, a commercially available yeast (trade name: Maurivin: Mauri Yeast Australia Pty, Limited) was added to the raw material suspension prepared as described above, and the yeast was subjected to saccharification, fermentation and culture at 30° C. under stirring at 120 rpm, and 1 ml of the reaction liquid was collected after each of 24 hours and 48 hours and was centrifuged for 5 minutes at 10,000 rpm. The enzyme activity of the supernatant obtained thereby was measured.

Example A18

100 g of crushed forest residues was introduced into 700 ml of water containing 20 g of 97.0% sodium sulfite and 1 g of caustic soda, and the forest residues were treated at 170° C. for 60 minutes. Subsequently, the mixture was ground with a refiner (clearance 0.5 mm). This product was dehydrated and washed with a screw press, and the resulting product was used as a substrate raw material.

The substrate raw material was added at a final concentration of 5%, CSL (corn steep liquor) was added at a final concentration of 1%, ammonium sulfate was added at a final concentration of 0.5%, and sodium chloride was added at a final concentration of 100 mM. Thus, 400 ml of a lignocellulose suspension having an electrical conductivity of 8.9 mS/cm was prepared.

The lignocellulose suspension prepared as described above was steam sterilized at 120° C. for 20 minutes and was cooled to 40° C. Subsequently, 10 ml of an enzyme (trade name: GC220; manufactured by Genencor International, Inc.) was added thereto.

A saccharification reaction was carried out at 30° C. under stirring at 120 rpm, and 1 ml of the reaction liquid was collected after each of 24 hours and 48 hours and was centrifuged for 5 minutes at 10,000 rpm. The enzyme activity of the supernatant obtained thereby was measured.

Example A19

100 g of crushed forest residues was introduced into 700 ml of water containing 20 g of 97.0% sodium sulfite and 1 g of caustic soda, and the forest residues were treated at 170° C. for 60 minutes. Subsequently, the mixture was ground with a refiner (clearance 0.5 mm). This product was dehydrated and washed with a screw press, and the resulting product was used as a substrate raw material.

The substrate raw material was added at a final concentration of 5%, CSL (corn steep liquor) was added at a final concentration of 1%, ammonium sulfate was added at a final concentration of 0.5%, and sodium chloride was added at a final concentration of 100 mM. Thus, 400 ml of a lignocellulose suspension having an electrical conductivity of 9.4 mS/cm was prepared.

The lignocellulose suspension prepared as described above was steam sterilized at 120° C. for 20 minutes and was cooled to 40° C. Subsequently, 10 ml of an enzyme (trade name: GC220; manufactured by Genencor International, Inc.) was added thereto.

Furthermore, a commercially available yeast (trade name: Maurivin: Mauri Yeast Australia Pty, Limited) was added to the raw material suspension prepared as described above, and the yeast was subjected to saccharification, fermentation and culture at 30° C. under stiffing at 120 rpm, and 1 ml of the reaction liquid was collected after each of 24 hours and 48 hours and was centrifuged for 5 minutes at 10,000 rpm. The enzyme activity of the supernatant obtained thereby was measured.

Example A20

The experiment was carried out in the same manner as in Example A16, except that 700 ml of water containing 20 g of 97.0% sodium sulfite and 1 g of caustic soda used was used instead of 1000 ml of water containing 20 g of 48% caustic soda used in the method of Example A16. The electrical conductivity in the reaction system at this time was 11.2 mS/cm.

Example A21

The experiment was carried out in the same manner as in Example A17, except that 700 ml of water containing 20 g of 97.0% sodium sulfite and 1 g of caustic soda used was used instead of 1000 ml of water containing 20 g of 48% caustic soda used in the method of Example A17. The electrical conductivity in the reaction system at this time was 11.2 mS/cm.

Comparative Example A1

The experiment was carried out in the same manner as in Example A1, except that instead of the sodium chloride added to a final concentration of 100 mM in the method of Example A1, sulfuric acid was added to adjust the electrical conductivity of the reaction system to 6.5 mS/cm.

Comparative Example A2

The experiment was carried out in the same manner as in Example A1, except that instead of the sodium chloride added to a final concentration of 100 mM in the method of Example A1, sodium hydroxide was added to adjust the electrical conductivity of the reaction system to 8.0 mS/cm.

Comparative Example A3

The experiment was carried out in the same manner as in Example 3, except that sodium chloride was not added in the method of Example A3. The electrical conductivity in the reaction system at this time was 4.2 mS/cm.

Comparative Example A4

The experiment was carried out in the same manner as in Example A3, except that instead of the sodium chloride added to a final concentration of 100 mM in the method of Example A3, sulfuric acid was added to adjust the electrical conductivity of the reaction system to 6.3 mS/cm.

Comparative Example A5

The experiment was carried out in the same manner as in Example A3, except that instead of the sodium chloride added to a final concentration of 100 mM in the method of Example A3, hydrochloric acid was added to adjust the electrical conductivity of the reaction system to 6.6 mS/cm.

Comparative Example A6

The experiment was carried out in the same manner as in Example A3 except that instead of the sodium chloride added to a final concentration of 100 mM in the method of Example A3, sodium hydroxide was added to adjust the electrical conductivity of the reaction system to 8.2 mS/cm.

Comparative Example A7

The experiment was carried out in the same manner as in Example A1, except that instead of the sodium chloride added to a final concentration of 100 mM in the method of Example A1, sodium chloride was added to a final concentration of 5 mM to adjust the electrical conductivity of the reaction system to 4.6 mS/cm.

The results of Examples A1 to A21 and Comparative Examples A1 to A7 are shown in Table A1.

TABLE A1

| Item | Electrical conductivity (mS/cm) | pH | Enzyme recovery ratio (%) After cultured for 24 hours | After cultured for 48 hours |
|---|---|---|---|---|
| Example A1 | 11.8 | 4.0 | 90.2 | 88.1 |
| Example A2 | 8.6 | 7.5 | 89.9 | 86.5 |
| Example A3 | 12.0 | 4.0 | 89.8 | 88.7 |
| Example A4 | 13.3 | 3.9 | 79.2 | 77.3 |
| Example A5 | 14.5 | 4.0 | 81.1 | 88.0 |
| Example A6 | 14.7 | 3.9 | 75.8 | 75.0 |
| Example A7 | 13.6 | 7.0 | 86.6 | 84.9 |
| Example A8 | 16.9 | 4.0 | 84.5 | 82.0 |
| Example A9 | 12.6 | 9.6 | 72.5 | 70.8 |
| Example A10 | 15.0 | 6.8 | 90.2 | 89.1 |
| Example A11 | 11.9 | 6.8 | 89.0 | 86.2 |
| Example A12 | 8.9 | 7.4 | 90.5 | 87.6 |
| Example A13 | 15.4 | 5.8 | 89.7 | 87.3 |
| Example A14 | 7.1 | 4.5 | 90.9 | 89.8 |
| Example A15 | 10.9 | 5.2 | 91.0 | 88.4 |
| Example A16 | 11.8 | 4.2 | 88.3 | 85.4 |
| Example A17 | 11.8 | 4.3 | 88.2 | 85.9 |
| Example A18 | 8.9 | 4.0 | 90.3 | 84.5 |
| Example A19 | 9.4 | 4.0 | 91.0 | 86.7 |
| Example A20 | 11.2 | 4.3 | 92.8 | 91.2 |
| Example A21 | 11.2 | 4.4 | 92.5 | 91.1 |
| Comp. Exe. A1 | 6.5 | 2.7 | 38.4 | 17.6 |
| Comp. Exe. A2 | 8.0 | 9.3 | 60.1 | 44.6 |
| Comp. Exe. A3 | 4.2 | 4.0 | 58.4 | 34.2 |
| Comp. Exe. A4 | 6.3 | 2.8 | 35.2 | 15.1 |
| Comp. Exe. A5 | 6.6 | 2.2 | 29.3 | 8.8 |
| Comp. Exe. A6 | 8.2 | 9.1 | 54.1 | 41.6 |
| Comp. Exe. A7 | 4.6 | 4.0 | 62.0 | 50.7 |

According to the results of Table A1, the method for the enzymatic saccharification treatment of a lignocellulose-based raw material of the Examples shows that when a lignocellulose-based raw material suspension in which a water-soluble salt has been added to an enzymatic saccharification reaction system and the electrical conductivity has been adjusted to a predetermined value range, is subjected to enzymatic saccharification, not only the enzyme recovery ratio from the saccharification treated liquid is high in the early stage, but also the enzyme recovery ratio is stable at a high level even after a lapse of time.

On the contrary, when the electrical conductivity is adjusted using sulfuric acid (Comparative Example A1, Comparative Example A4), hydrochloric acid (Comparative Example A5), or sodium hydroxide (Comparative Example A2, Comparative Example A6) without adding a water-soluble salt to the enzymatic saccharification reaction system, the enzyme recovery ratio from the saccharification treated liquid is low in the early stage, and the decrease in the recovery ratio after a lapse of time is also significant. Furthermore, even in the case where the electrical conductivity of the enzyme reaction system is low (Comparative Example A3, Comparative example A7) without or with adding a salt, the enzyme recovery ratio from the saccharification treated liquid is low in the early stage, and is further decreased after a lapse of time.

Example B1

The production of ethanol was carried out by the process flow shown in FIG. 3.

[Pretreatment]

Chipped bark of *Eucalyptus globulus* was crushed with a single-screw crusher equipped with a 20-mm round hole screen (manufactured by Seiho Kiko Co., Ltd., SC-15) and was used as a raw material.

A calcium hydroxide solution suspended calcium hydroxide in water was added to the raw material to a concentration of 12.5 mass % relative to 100 kg (absolute dry weight) of the raw material (liquid ratio to the raw material 8), and then the mixture was heated at 120° C. for 1 hour (alkali treatment). The raw material after the alkali treatment was ground with a refiner (manufactured by Kumagai Riki Kogyo Co., Ltd., KRK High Concentration Disk Refiner: clearance 0.5 mm). An equal amount of pure water was added to the raw material after the grinding treatment, and then the mixture was adjusted to pH 5 using sulfuric acid under stirring. Subsequently, the mixture was subjected to solid-liquid separation (dehydration) using a 20-mesh (847 µm) screen, and then the solid was washed with water until the electrical conductivity of the solution reached 30 µS/cm. The solid obtained after the solid-liquid separation (pretreated product) was supplied as a raw material to the saccharification fermentation step.

[Primary Parallel Saccharifying Fermentation]

100 kg (absolute dry weight) of the raw material, 5 g/L of polypeptone, 3 g/L of a yeast extract, and 3 g/L of a wheat germ extract were respectively added to the primary parallel saccharifying fermentation tank so that the raw material concentration would be 10 mass %, and then water was added thereto to adjust the final volume to 1 m³. A culture fluid containing yeast cells that had been precultured in 50 L of a liquid medium (glucose 30 g/L, polypeptone 5 g/L, yeast extract 3 g/L, wheat germ extract 3 g/L, pH 5.6) at 30° C. for 24 hours, and 50 L of a commercially available cellulase (Accellerase DUET, manufactured by Genencor International, Inc.) were added to the fermentation tank, and primary parallel saccharifying fermentation was carried out at 30° C. for 24 hours. The pH of the culture fluid during the saccharifying fermentation was adjusted to 5.0.

[Solid-Liquid Separation]

The culture fluid obtained by the primary parallel saccharifying fermentation was subjected to solid-liquid separation with a screw press (SHX-200×1500 L, manufactured by Fukoku Kogyo Co., Ltd., screen size 1.2 mm), and a residue (primary residue) and a filtrate were separated. The primary residue thus recovered was 19.4 kg (absolute dry weight).

[Sieve Treatment]

The filtrate obtained after the solid-liquid separation was passed through a 400-mesh (39 µm) screen, and thereby fine fibers in the culture fluid were recovered. The amount of recovered fine fibers thus obtained was 15.6 kg (absolute dry weight) in total. The entire amount (15.6 kg) of the recovered fine fibers was conveyed to the primary parallel saccharifying fermentation tank.

[Ethanol Production]

The filtrate obtained by the sieve treatment was separated into an aqueous solution containing ethanol and a concentrated culture fluid using a reduced pressure distillation apparatus (Evapor CEP-1, Okawara Corp.) under the conditions of distillation temperature: 40° C., heating temperature: 80° C., and the amount of fed liquid: 150 L/h. The volume and ethanol concentration of the aqueous solution containing ethanol thus obtained were measured, and the amount of recovered ethanol was calculated. The ethanol concentration in the solution was measured with a glucose sensor (Model BF-400, manufactured by Oji Scientific Instruments Co., Ltd.).

[Centrifugation]

The concentrated culture fluid separated from the reduced pressure distillation apparatus was separated into a residue (secondary residue) and a filtrate by operating a decanter type centrifuge (manufactured by IHI Corp., Model HS-204L) at a speed of rotation of 4500 rpm and a differential velocity of 5.0 rpm. The filtrate was conveyed to the primary parallel saccharifying fermentation tank. 18.6 kg (absolute dry weight) of the secondary residue was recovered.

Example B2

The production of ethanol was carried out by the production flow shown in FIG. 4.

[Pretreatment]

The pretreatment was carried out by the same method as that used in Example B1.

[Primary Parallel Saccharifying Fermentation]

The primary parallel saccharifying fermentation was carried out by the same method as that used in Example B1.

[Solid-Liquid Separation]

The solid-liquid separation was carried out by the same method as that used in Example B1. 19.2 kg (absolute dry weight) of the primary residue was recovered.

[Sieve Treatment]

The sieve treatment was carried out by the same method as that used in Example B1. The amount of recovered fine fibers obtained by subjecting 100 kg in total of the raw material to primary parallel saccharifying fermentation was 15.5 kg (absolute dry weight) in total.

[Secondary Parallel Saccharifying Fermentation]

15.5 kg (absolute dry weight) of the fine fibers obtained by the sieve treatment was introduced to the secondary parallel saccharifying fermentation tank as a raw material. 5 g/L of polypeptone, 3 g/L of a yeast extract, and 3 g/L of a wheat germ extract were respectively introduced to the secondary parallel saccharifying fermentation tank, and the final volume was adjusted to 150 L with water. A commercially available yeast (trade name: Maurivin: Mauri Yeast Australia Pty Limited) was cultured in 50 L of a liquid medium (glucose 30 g/L, polypeptone 5 g/L, yeast extract 3 g/L, wheat germ extract 3 g/L, pH 5.6) at 30° C. for 24 hours. 50 L of the culture fluid containing yeast obtained after the culture, and 10 L of a commercially available cellulase (Accellerase DUET, manufactured by Genencor International, Inc.) were introduced to the fermentation tank, and secondary parallel saccharifying fermentation was carried out at 30° C. for 24 hours. The pH of the culture fluid during the saccharification fermentation was adjusted to 5.0.

[Ethanol Production]

The ethanol production was carried out by the same method as that used in Example B1.

[Centrifugation]

The centrifugation was carried out by the same method as that used in Example B1. 18.6 kg (absolute dry weight) of the secondary residue was recovered.

Comparative Example B1

Figure 5:
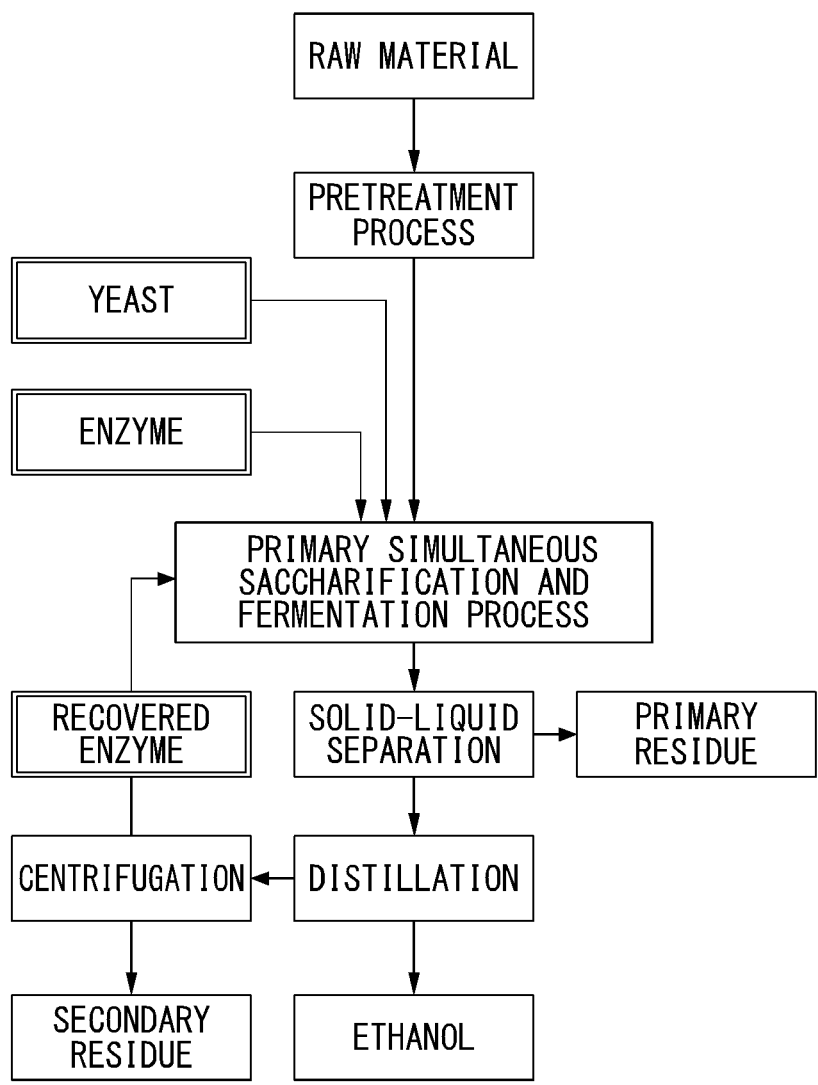
FIG. 5 is a diagram showing the production process flow of Comparative Example B1.

The production of ethanol was carried out by the process flow shown in FIG. 5. A test excluding the [Sieve treatment] of Example B1 was carried out as Comparative Example B1 (described below).

[Pretreatment]

The pretreatment was carried out by the same method as that used in Example B1.

[Primary Parallel Saccharifying Fermentation]

The primary parallel saccharifying fermentation was carried out by the same method as that used in Example B1.

[Solid-Liquid Separation]

The solid-liquid separation was carried out by the same method as that used in Example B1. 19.3 kg (absolute dry weight) of the primary residue was recovered.

[Ethanol Production]

The filtrate obtained by the solid separation was separated into an aqueous solution containing ethanol and a concentrated culture fluid by the same method as described in Example B1. The volume and ethanol concentration of the aqueous solution containing ethanol thus obtained were measured, and the amount of recovered ethanol was calculated.

[Centrifugation]

The centrifugation was carried out by the same method as that used in Example B1. 34.2 kg (absolute dry weight) of the secondary residue was recovered.

TABLE B1

|  | Ethanol production (kg) |
| --- | --- |
| Example B1 | 13.9 |
| Example B2 | 14.1 |
| Comparative Example B1 | 10.5 |

The results of the ethanol production are shown in Table B1. In Example B1 (the case in which fine fibers were recovered and conveyed to the primary parallel saccharifying fermentation tank) and Example B2 (the case in which fine fibers were recovered and conveyed to the secondary parallel saccharifying fermentation tank), the ethanol production was increased as compared with Comparative Example B1 (the case in which fine fibers were not recovered).

Example B3

Saccharification Fermentation Test

A saccharification fermentation test was carried out in a test tube using the fine fibers obtained in Example B1 as a raw material, and the ethanol production was measured by the method described below.

A commercially available yeast (trade name: Maurivin: Mauri Yeast Australia Pty Limited) was cultured in a medium prepared by mixing 100 ml of liquid medium A (polypeptone 5 g/L, yeast extract 3 g/L, wheat germ extract 3 g/L, glucose 30 g/L, dissolved in distilled water, pH 5.6) and 20 ml of liquid medium B (polypeptone 15 g/L, yeast extract 10 g/L, wheat germ extract 10 g/L: dissolved in distilled water) at 30° C. for 24 hours. 100 ml of the culture fluid obtained after the culture was centrifuged (5000 rpm, for 20 minutes), and the supernatant was removed. The volume of the residual culture fluid was adjusted to 10 ml (the yeast cells were collected) (concentrated yeast cells).

The raw material (fine fibers) was introduced into a conical flask having a capacity of 300 ml, to a final concentration of 5 mass %. Subsequently, 10 ml of the concentrated yeast cells and 2.5 ml of a commercially available cellulase (Accellerase DUET, manufactured by Genencor International, Inc.) were added thereto, and the final volume was made up to 100 ml with distilled water. This liquid mixture was cultured at 30° C. for 24 hours (saccharification fermentation). The culture fluid obtained after the culture was centrifuged (5000 rpm, for 20 minutes), and the ethanol concentration in the supernatant was measured. Furthermore, the Kappa number (index of lignin content) of the fine fibers was measured by a measurement method equivalent to JIS P8211.

Comparative Example B2

A saccharification fermentation test was carried out by the same method as that used in Example B3, using the primary residue obtained in Example B1 as a raw material. The ethanol output and the Kappa number of the primary residue were measured.

Comparative Example B3

A saccharification fermentation test was carried out by the same method as that used in Example B3, using the secondary residue obtained in Example B1 as a raw material. The ethanol output and the Kappa number of the secondary residue were measured.

TABLE B2

|  | Ethanol concentration (%) | Kappa number |
|---|---|---|
| Example B3 (fine fibers) | 0.58 | 145 |
| Comparative Example B2 (primary residue) | 0.10 | 247 |
| Comparative Example B3 (secondary residue) | 0.23 | 315 |

The ethanol concentrations and the Kappa numbers are shown in Table B2. When the fine fibers (Example B3) were used as the raw material, the ethanol concentration in the culture fluid was higher as compared with the cases of using the primary residue (Comparative Example B2) and the secondary residue (Comparative Example B3) as the raw material. Furthermore, the Kappa number of the fine fibers (Example B3) had a lower value as compared with the Kappa numbers of the primary residue (Comparative Example B2) and the secondary residue (Comparative Example B3). From the results described above, it was found that the fine fibers had a low lignin content as compared with the primary residue and the secondary residue, and as a result, when the fine fibers were used as the raw material for saccharification fermentation, the ethanol output increased as compared with the primary residue and the secondary residue. The fine fibers allow the saccharification fermentation to proceed easily, even if the fine fibers are not pretreated (mechanical treatment or the like), and thus it was found that the fine fibers are suitable as the raw material for saccharification fermentation.

Example B4

A test in which the forest residues of *Eucalyptus globulus* (bark 70%, branches and leaves 30%) was used as the raw material, instead of the bark of *Eucalyptus globulus* used as the raw material in Example B1, was carried out as Example B4.

The test was carried out entirely in the same manner as in Example B1, except that forest residues were used (the process flow was the same as shown in FIG. 1).

Comparative Example B4

A test in which the [Sieve treatment] of Example B4 was omitted, was carried out as Comparative Example B4. The test was carried out entirely in the same manner as in Example B4, except that the sieve treatment was omitted (the process flow was the same as shown in FIG. 5).

TABLE B3

|  | Ethanol output (kg) |
|---|---|
| Example B4 | 12.4 |
| Comparative Example B4 | 10.2 |

The results of the ethanol output are shown in Table B3. In Example B4 (the case in which the fine fibers were collected and conveyed to the primary parallel saccharifying fermentation tank), the ethanol output increased as compared with Comparative Example B4 (the case in which the fine fibers were not recovered).

Example B5

Figure 6:
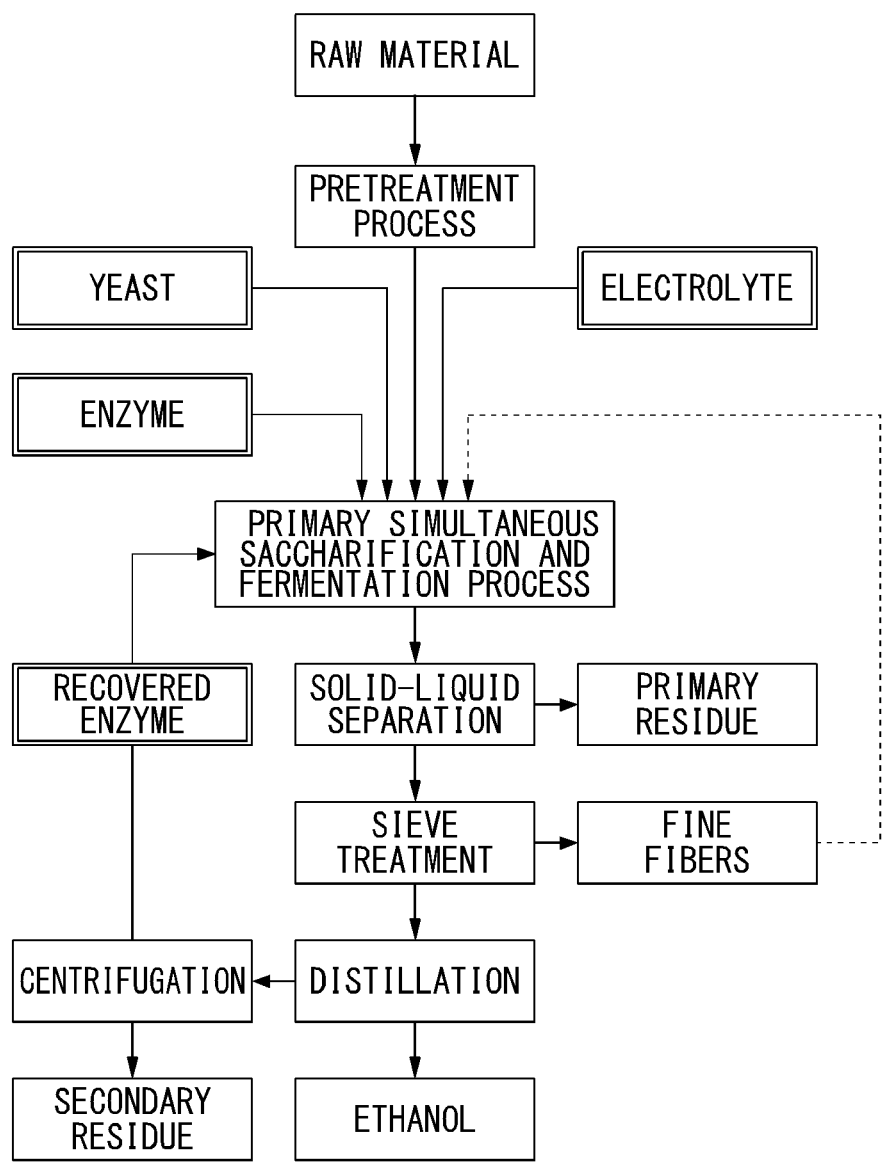
FIG. 6 is a diagram showing the production process flow of Example B5.

The production of ethanol was carried out by the process flow shown in FIG. 6.

[Pretreatment]

The pretreatment was carried out in the same manner as in Example B1.

[Primary Parallel Saccharifying Fermentation]

The primary parallel saccharifying fermentation was carried out by the same method as that used in Example B1, except that sodium chloride was added as an electrolyte to the culture fluid. Sodium chloride (electrolyte) was added to the culture fluid that had been adjusted by the same method as that used in Example B1, to a final concentration of 100 mM (electrical conductivity of the raw material suspension: 12.2 mS/cm). Subsequently, yeast cells and a commercially available cellulase were introduced to the fermentation tank by the same method as that used in Example B1, and thus the primary parallel saccharifying fermentation was carried out.

[Solid-Liquid Separation]

The solid-liquid separation was carried out by the same method as that used in Example B1. 15.3 kg (absolute dry weight) of the primary residue was recovered.

[Sieve Treatment]

The sieve treatment was carried out by the same method as that used in Example B1. 13.4 kg (absolute dry weight) in total of the fine fibers were recovered. The entire amount (13.4 kg) of the recovered fine fibers was conveyed to the primary parallel saccharifying fermentation tank.

[Ethanol Production]

The ethanol production was carried out by the same method as that used in Example B1.

[Centrifugation]

The centrifugation was carried out by the same method as that used in Example B1. 14.7 kg (absolute dry weight) of the secondary residue was recovered.

TABLE B4

|  | Ethanol output (kg) |
|---|---|
| Example B5 | 14.3 |

The results of the ethanol output are shown in Table B4. In the case of adding sodium chloride to the culture fluid (Example B5), the ethanol output increased as compared with the case in which sodium chloride was not added (Example B1).

Example B6

Figure 7:
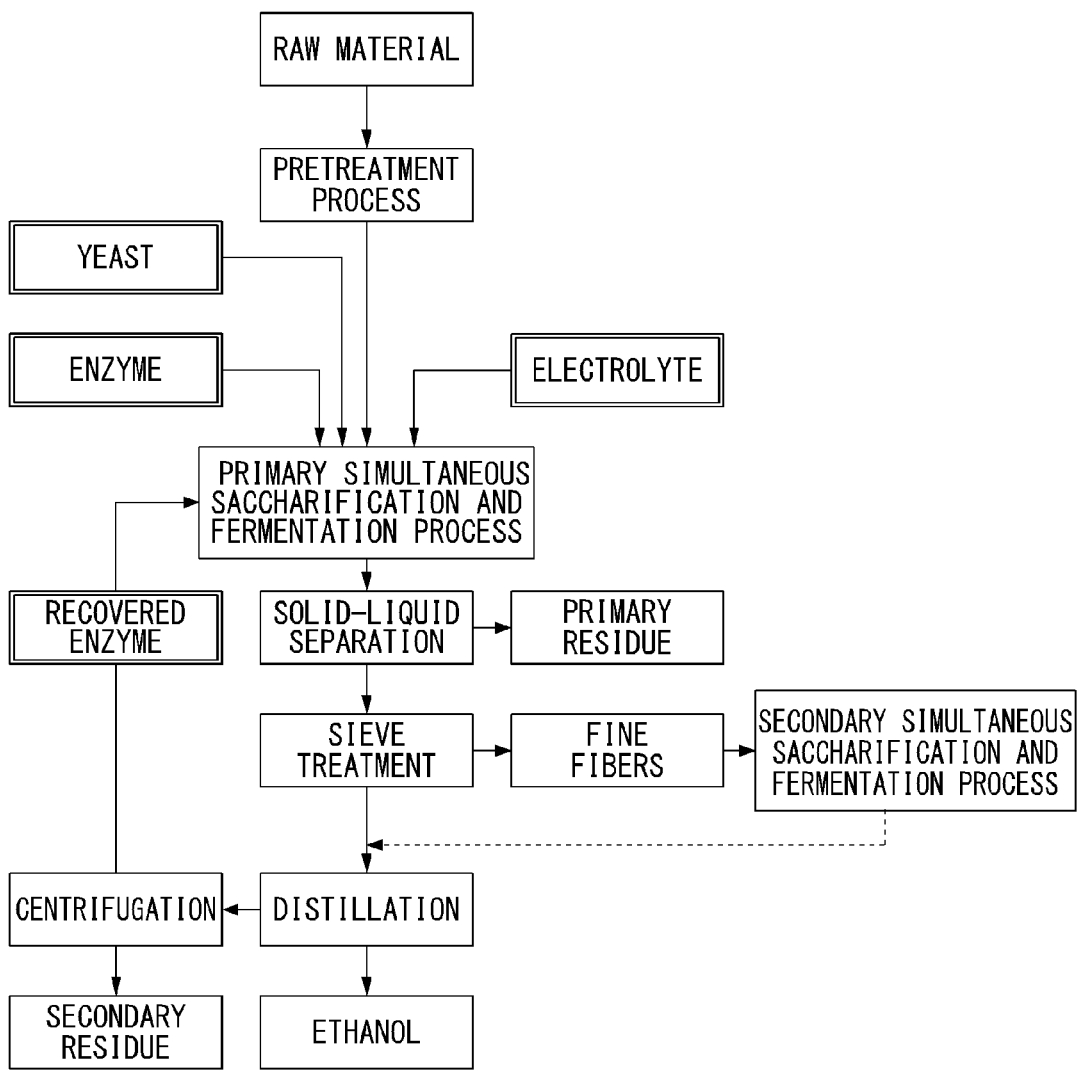
FIG. 7 is a diagram showing the production process flow of Example B6.

The production of ethanol was carried out by the same process flow shown in FIG. 7.

[Pretreatment]

The pretreatment was carried out in the same manner as in Example B1.

[Primary Parallel Saccharifying Fermentation]

The primary parallel saccharifying fermentation was carried out by the same method as that used in Example B1, except that sodium chloride was added as an electrolyte to the culture fluid. Sodium chloride (electrolyte) was added to the culture fluid that had been adjusted by the same method as that used in Example B1, to a final concentration of 100 mM (electrical conductivity of the raw material suspension: 12.2 mS/cm). Subsequently, yeast cells and a commercially available cellulase were introduced to the fermentation tank by the same method as that used in Example B1, and thus the primary parallel saccharifying fermentation was carried out.

[Solid-Liquid Separation]

The solid-liquid separation was carried out by the same method as that used in Example B1. 14.8 kg (absolute dry weight) of the primary residue was recovered.

[Sieve Treatment]

The sieve treatment was carried out by the same method as that used in Example B1. 13.0 kg (absolute dry weight) in total of the fine fibers were recovered. The entire amount (13.0 kg) of the recovered fine fibers was conveyed to the primary parallel saccharifying fermentation tank.

[Secondary Parallel Saccharifying Fermentation]

The secondary parallel saccharifying fermentation was carried out by the same method as that used in Example B2.

[Ethanol Production]

The ethanol production was carried out by the same method as that used in Example B1.

[Centrifugation]

The centrifugation was carried out by the same method as that used in Example B1. 14.2 kg (absolute dry weight) of the secondary residue was recovered.

TABLE B5

| | Ethanol output (kg) |
|---|---|
| Example B6 | 14.5 |

The results of the ethanol output are shown in Table 5. In the case of adding sodium chloride to the culture fluid (Example B6), the ethanol output increased as compared with the case in which sodium chloride was not added (Example B2).

Industrial Applicability

According to the enzymatic saccharification treatment method of the present invention, the adsorption of saccharification enzymes to the unreacted components or reaction residue of a lignocellulose-based raw material is suppressed, the separation of enzymes from the enzymatic saccharification treated liquid is facilitated, and the recycling ratio of saccharification enzymes is maintained at a high level for a long time period during the enzymatic saccharification treatment process. Therefore, it is possible to industrially produce saccharides, ethanol and the like by the enzymatic saccharification treatment of a lignocellulose-based raw material.

Furthermore, according to the present invention, the ethanol output can be increased by reusing the fine fibers included in the culture fluid obtained after the saccharification fermentation, as a raw material of saccharification fermentation. Furthermore, the ethanol output can be increased by adding an electrolyte to the culture fluid.

The invention claimed is:

1. A method for an enzymatic saccharification treatment of a lignocellulose-based raw material, comprising:
adding the lignocellulose-based raw material, which has been subjected to a pretreatment for making the raw material appropriate for an enzymatic saccharification reaction, and an electrolyte containing a water-soluble salt to water containing a cellulose saccharification enzyme, thereby preparing a raw material suspension whose electrical conductivity has been adjusted to 7.1 mS/cm to 16.9 mS/cm;
performing the enzymatic saccharification treatment by subjecting the raw material suspension to an enzymatic saccharification reaction while maintaining the electrical conductivity of the raw suspension within the range of 7.1 mS/cm to 16.9 mS/cm;
separating and recovering the reaction product and an enzyme-containing solution from the treated suspension after the enzymatic saccharification treatment; and
recycling the recovered enzyme-containing solution as the enzyme for the enzymatic saccharification treatment, wherein
the pretreatment includes immersing the lignocellulose-based raw material in a solution containing an alkali selected from sodium hydroxide, potassium hydroxide, calcium hydroxide, sodium carbonate and sodium hydrogen carbonate, or a mixture thereof, or a mixture of sodium sulfite and said alkali,
the lignocellulose-based raw material is forest residues or tree bark, and
the water-soluble salt is at least one water-soluble salt selected from the group consisting of alkali metal salts and alkaline earth metal salts.

2. The method according to claim 1, wherein the water-soluble salt is a salt selected from the group consisting of halides, sulfates, sulfites, thiosulfates, carbonates, hydrogen carbonates, phosphates, dihydrogen phosphates, hydrogen diphosphates, acetates, and citrates of alkali metals and alkaline earth metals.

3. A method for an enzymatic saccharification treatment of a lignocellulose-based raw material, comprising:
a pretreatment step of subjecting the lignocellulose-based raw material to a treatment for making the lignocellulose-based raw material appropriate for an enzymatic saccharification reaction;
an enzymatic saccharification treatment step of adding the pretreated lignocellulose-based raw material and an electrolyte containing a water-soluble salt to water containing a cellulose saccharification enzyme, thereby preparing a raw material suspension whose electrical conductivity has been adjusted to 7.1 mS/cm to 16.9 mS/cm, and subjecting the raw material suspension to the enzymatic saccharification reaction while maintaining the electrical conductivity of the raw suspension within the range 7.1 mS/cm to 16.9 mS/cm;
a solid-liquid separation step of removing a solid residue from a treated suspension resulting from the enzymatic saccharification treatment step;
a centrifugation step of centrifuging a liquid fraction resulting from the solid-liquid separation step, thereby obtaining a liquid fraction containing the enzymes and in which a remaining residue has been removed;
a membrane separation step of separating the liquid fraction resulting from the centrifugation step into an enzyme-containing solution and a saccharide-containing solution; and
an enzyme recycling step of recycling and supplying the enzyme-containing solution resulting from the membrane separation step to the enzyme saccharification treatment step as an enzyme source, wherein the lignocellulose-based raw material is subjected to the enzymatic saccharification treatment through a series of the steps, wherein the pretreatment step includes immersing the lignocellulose-based raw material in a solution containing an alkali selected from sodium hydroxide, potassium hydroxide, calcium hydroxide, sodium carbonate and sodium hydrogen carbonate, or a mixture thereof, or a mixture of sodium sulfite and said alkali, the lignocellulose-based raw material is forest residues or tree bark, and the water-soluble salt is at least one water-soluble salt selected from the group consisting of alkali metal salts and alkaline earth metal salts.

4. The method according to claim 3, wherein the enzymatic saccharification treatment step is a simultaneous saccharification and fermentation treatment step in which the enzymatic saccharification treatment of the lignocellulose-based raw material and a fermentation treatment of the resulting saccharides are performed in combination by using a cellulase preparation and a microorganism for fermentation which uses the saccharides as a fermentation substrate, thereby producing a fermentation product together with the saccharides.

5. The method according to claim 4, further comprising:
a distillation step of separating and recovering the fermentation product from the liquid fraction resulting from the solid-liquid separation step through distillation,
wherein the centrifugation step is performed by centrifuging a residual distillate resulting from the distillation step, thereby obtaining the liquid fraction containing the enzymes and the saccharides in which the remaining residue has been removed, and
the lignocellulose-based raw material is subjected to a simultaneous saccharification and fermentation treatment through a series of the steps.

6. The method according to claim 5, wherein the saccharide-containing solution separated and recovered from the membrane separation step is a liquid containing the saccharides which includes oligosaccharides as main components.

7. The method according to claim 5, wherein the liquid fraction resulting from the centrifugation step is recycled and supplied to the enzymatic saccharification treatment as an enzyme-containing solution containing the saccharides, without going through the membrane separation step.

8. A method for an enzymatic saccharification treatment of a lignocellulose-based raw material comprising:
a pretreatment step of subjecting a lignocellulose-based raw material to a treatment for making the lignocellulose-based raw material appropriate for an enzymatic saccharification reaction;
a simultaneous saccharification and fermentation treatment step of adding the pretreated lignocellulose-based raw material, a microorganism for fermentation which uses saccharides as a fermentation substrate, and an electrolyte containing a water-soluble salt to water containing a cellulose saccharification enzyme, thereby preparing a raw material suspension whose electrical conductivity has been adjusted to 7.1 mS/cm to 16.9 mS/cm, and subjecting the raw material suspension to both of the enzymatic saccharification treatment and a fermentation treatment of using the resulting saccharides as a substrate while maintaining the electrical conductivity of the raw suspension within the range of 7.1 mS/cm to 16.9 mS/cm;

a solid-liquid separation step of separating a treated suspension resulting from the simultaneous saccharification and fermentation treatment step into a residue and a liquid fraction using a screw press having a screen size of 1.0 mm to 2.0 mm;

a sieve treatment step of separating the liquid fraction resulting from the solid-liquid separation step into fine fibers and a liquid fraction through a sieve treatment using an 80- to 600-mesh sieve;

a distillation step of separating and recovering a fermentation product from the liquid fraction, in which fine fibers have been excluded by the sieve treatment, through distillation;

a centrifugation step of centrifuging a residual distillate resulting from the distillation step to remove any remaining residue, thereby obtaining a liquid fraction containing the enzymes and the saccharides; and a recycling step of recycling and supplying the liquid fraction resulting from the centrifugation step to the simultaneous saccharification and fermentation treatment step as an enzyme-containing solution containing the saccharides, without going through a membrane separation, wherein the lignocellulose-based raw material is subjected to a simultaneous saccharification and fermentation treatment through a series of the steps, wherein the pretreatment includes immersing the lignocellulose-based raw material in a solution containing an alkali selected from sodium hydroxide potassium hydroxide, calcium hydroxide, sodium carbonate and sodium hydrogen carbonate, or a mixture thereof, or a mixture of sodium sulfite and said alkali, the lignocellulose-based raw material is forest residues or tree bark, and the water-soluble salt is at least one water-soluble salt selected from the group consisting of alkali metal salts and alkaline earth metal salts.

* * * * *